United States Patent
Chen et al.

(10) Patent No.: US 11,029,306 B2
(45) Date of Patent: Jun. 8, 2021

(54) NANOPORE-BASED SEQUENCING USING VOLTAGE MODE WITH HYBRID MODE STIMULI

(71) Applicant: Roche Sequencing Solutions, Inc., Pleasanton, CA (US)

(72) Inventors: Roger J. A. Chen, Saratoga, CA (US); Hui Tian, Cupertino, CA (US); J. William Maney, Jr., Emerald Hills, CA (US)

(73) Assignee: Roche Sequencing Solutions, Inc., Pleasanton, CA (US)

( * ) Notice: Subject to any disclaimer, the term of this patent is extended or adjusted under 35 U.S.C. 154(b) by 0 days.

(21) Appl. No.: 16/297,428

(22) Filed: Mar. 8, 2019

(65) Prior Publication Data

US 2019/0204295 A1    Jul. 4, 2019

Related U.S. Application Data

(63) Continuation of application No. PCT/EP2017/073095, filed on Sep. 14, 2017.

(Continued)

(51) Int. Cl.
  *G01N 33/487*  (2006.01)
  *C12Q 1/6869*  (2018.01)
  *G01N 27/447*  (2006.01)

(52) U.S. Cl.
  CPC ..... *G01N 33/48721* (2013.01); *C12Q 1/6869* (2013.01); *G01N 27/44713* (2013.01)

(58) Field of Classification Search
  CPC ....... G01N 33/48721; G01N 27/44713; C12Q 1/6869; C12Q 2565/631; C12Q 2565/629
  See application file for complete search history.

(56) References Cited

U.S. PATENT DOCUMENTS

2013/0244340 A1*  9/2013  Davis ............... G01N 33/48721
                                                                           436/501
2015/0111779 A1*  4/2015  Davis .................. C12Q 1/6816
                                                                           506/9

FOREIGN PATENT DOCUMENTS

WO    2016/099673 A1    6/2016
WO    2016/100749 A1    6/2016
(Continued)

OTHER PUBLICATIONS

International Search Report and Written Opinion dated Nov. 7, 2017 in corresponding PCT application No. PCT/EP2017/073095.

*Primary Examiner* — Luan V Van
*Assistant Examiner* — Caitlyn Mingyun Sun
(74) *Attorney, Agent, or Firm* — Roche Sequencing Solutions, Inc.

(57) ABSTRACT

A liquid voltage is applied to a first side of a lipid bilayer. The liquid voltage comprises a tag-reading period with a tag-reading voltage that tends to capture a tag into a nanopore in the lipid bilayer and an open-channel period with an open-channel voltage that tends to repel the tag. A pre-charging voltage source is connected to an integrating capacitor and a working electrode on a second side of the lipid bilayer during a pre-charging time period, such that the integrating capacitor and the working electrode are charged to a pre-charging voltage. The pre-charging voltage source is disconnected from the integrating capacitor and the working electrode during an integrating time period, such that a voltage of the integrating capacitor and a voltage of the working electrode may vary as a current flows through the nanopore. The pre-charging time period overlaps with a beginning portion of the tag-reading period.

13 Claims, 15 Drawing Sheets

Related U.S. Application Data

(60) Provisional application No. 62/394,903, filed on Sep. 15, 2016.

(56) References Cited

FOREIGN PATENT DOCUMENTS

| WO | 2017220732 A1 | 12/2017 |
| WO | 2018002005 A1 | 1/2018 |
| WO | 2018029108 A1 | 2/2018 |

\* cited by examiner

NANOPORE-BASED SEQUENCING USING VOLTAGE MODE WITH HYBRID MODE STIMULI

CROSS REFERENCE TO RELATED APPLICATIONS

This application is a continuation of International Patent Application No. PCT/EP2017/073095, filed Sep. 14, 2017, which claims priority to U.S. Provisional Application No. 62/394,903, filed Sep. 15, 2016, each of which is herein incorporated by reference in its entirety.

BACKGROUND OF THE INVENTION

Advances in micro-miniaturization within the semiconductor industry in recent years have enabled biotechnologists to begin packing traditionally bulky sensing tools into smaller and smaller form factors, onto so-called biochips. It would be desirable to develop techniques for biochips that make them more robust, efficient, and cost-effective.

BRIEF DESCRIPTION

Brief Description of the Drawings

Various embodiments of the invention are disclosed in the following detailed description and the accompanying drawings.

DETAILED DESCRIPTION

The invention can be implemented in numerous ways, including as a process; an apparatus; a system; a composition of matter; a computer program product embodied on a computer readable storage medium; and/or a processor, such as a processor configured to execute instructions stored on and/or provided by a memory coupled to the processor. In this specification, these implementations, or any other form that the invention may take, may be referred to as techniques. In general, the order of the steps of disclosed processes may be altered within the scope of the invention. Unless stated otherwise, a component such as a processor or a memory described as being configured to perform a task may be implemented as a general component that is temporarily configured to perform the task at a given time or a specific component that is manufactured to perform the task. As used herein, the term 'processor' refers to one or more devices, circuits, and/or processing cores configured to process data, such as computer program instructions.

A detailed description of one or more embodiments of the invention is provided below along with accompanying figures that illustrate the principles of the invention. The invention is described in connection with such embodiments, but the invention is not limited to any embodiment. The scope of the invention is limited only by the claims and the invention encompasses numerous alternatives, modifications and equivalents. Numerous specific details are set forth in the following description in order to provide a thorough understanding of the invention. These details are provided for the purpose of example and the invention may be practiced according to the claims without some or all of these specific details. For the purpose of clarity, technical material that is known in the technical fields related to the invention has not been described in detail so that the invention is not unnecessarily obscured.

Nanopore membrane devices having pore sizes on the order of one nanometer in internal diameter have shown promise in rapid nucleotide sequencing. When a voltage potential is applied across a nanopore immersed in a conducting fluid, a small ion current attributed to the conduction of ions through the nanopore can be observed. The size of the current is sensitive to the pore size.

A nanopore based sequencing chip may be used for nucleic acid (e.g., DNA) sequencing. A nanopore based sequencing chip incorporates a large number of sensor cells configured as an array. For example, an array of one million cells may include 1000 rows by 1000 columns of cells.

Figure 1:
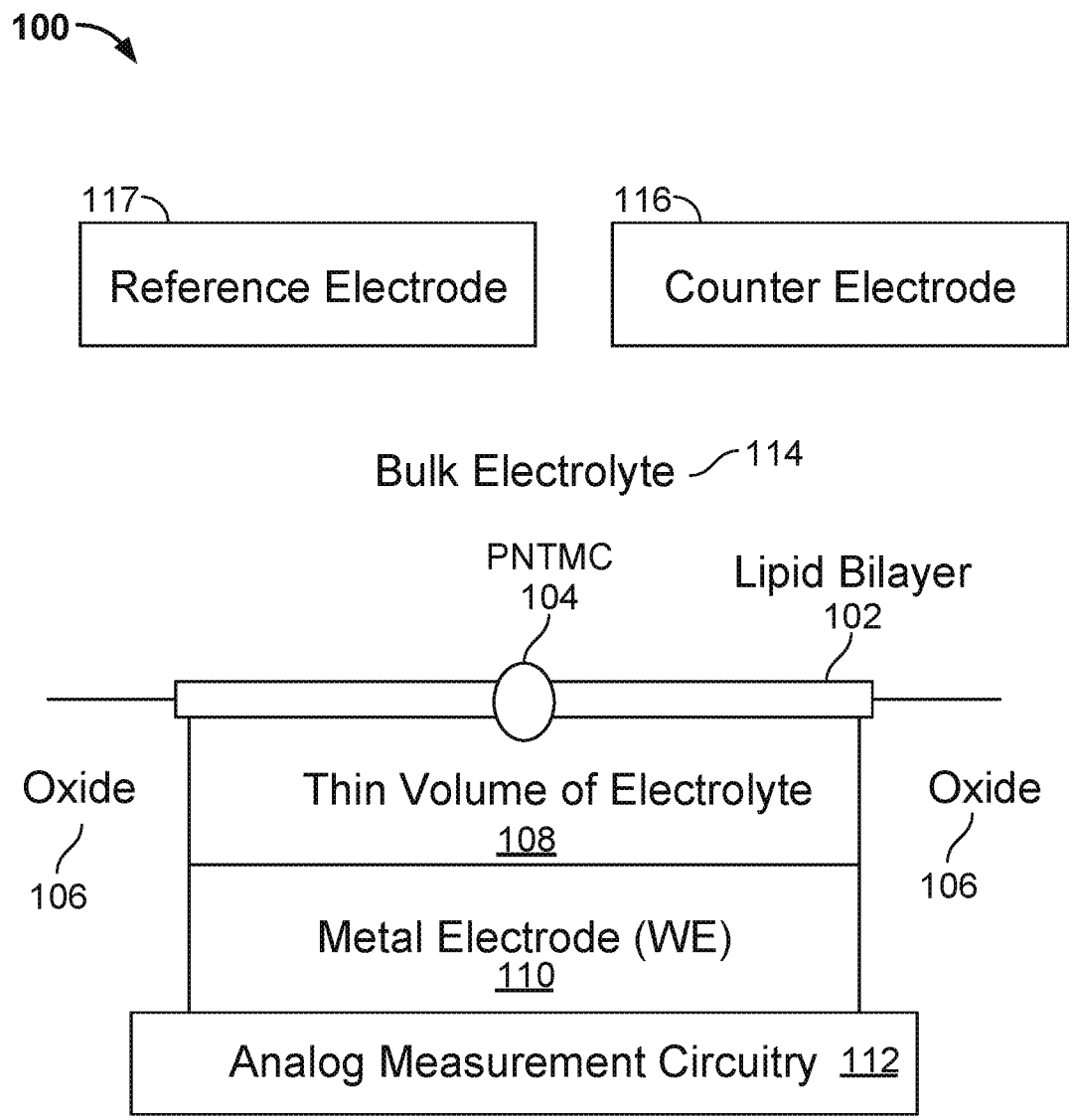
FIG. 1 illustrates an embodiment of a cell 100 in a nanopore based sequencing chip.

FIG. 1 illustrates an embodiment of a cell 100 in a nanopore based sequencing chip. A membrane 102 is formed over the surface of the cell. In some embodiments, membrane 102 is a lipid bilayer. The bulk electrolyte 114 containing soluble protein nanopore transmembrane molecular complexes (PNTMC) and the analyte of interest is placed directly onto the surface of the cell. In one embodiment, a single PNTMC 104 is inserted into membrane 102 by electroporation. The individual membranes in the array are neither chemically nor electrically connected to each other. Thus, each cell in the array is an independent sequencing machine, producing data unique to the single polymer molecule associated with the PNTMC. PNTMC 104 operates on the analytes and modulates the ionic current through the otherwise impermeable bilayer.

With continued reference to FIG. 1, analog measurement circuitry 112 is connected to a metal electrode 110 covered by a volume of electrolyte 108. The volume of electrolyte 108 is isolated from the bulk electrolyte 114 by the ion-impermeable membrane 102. PNTMC 104 crosses membrane 102 and provides the only path for ionic current to flow from the bulk liquid to working electrode 110. The cell also includes a counter electrode (CE) 116, which is in electrical contact with the bulk electrolyte 114. The cell may also include a reference electrode 117.

Figure 2:
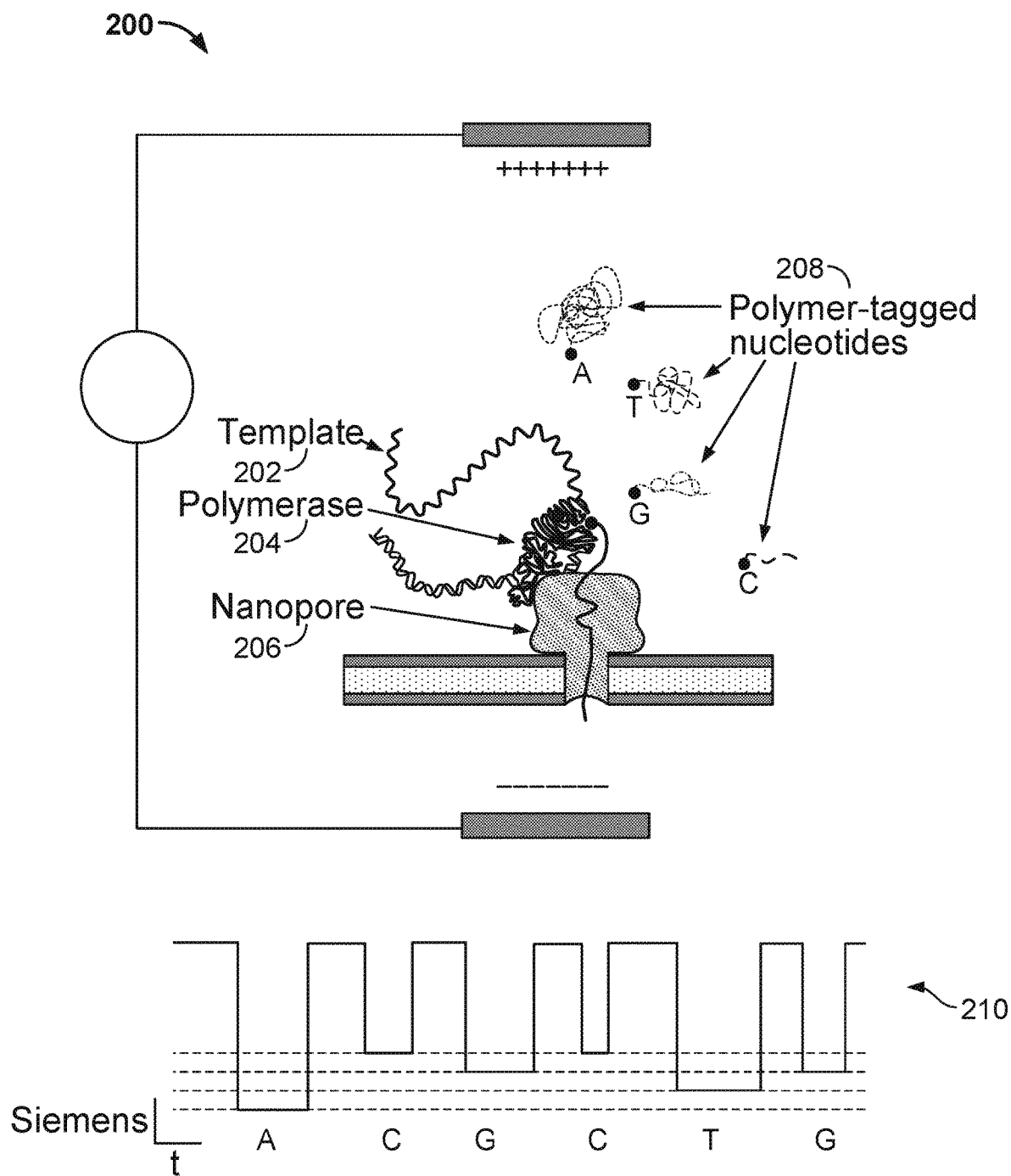
FIG. 2 illustrates an embodiment of a cell 200 performing nucleotide sequencing with the Nano-SBS technique.

In some embodiments, a nanopore array enables parallel sequencing using the single molecule nanopore-based sequencing by synthesis (Nano-SBS) technique. FIG. 2 illustrates an embodiment of a cell 200 performing nucleotide sequencing with the Nano-SBS technique. In the Nano-SBS technique, a template 202 to be sequenced and a primer are introduced to cell 200. To this template-primer complex, four differently tagged nucleotides 208 are added to the bulk aqueous phase. As the correctly tagged nucleotide is complexed with the polymerase 204, the tail of the tag is positioned in the barrel of nanopore 206. The tag held in the barrel of nanopore 206 generates a unique ionic blockade signal 210, thereby electronically identifying the added base due to the tags' distinct chemical structures.

Figure 3:
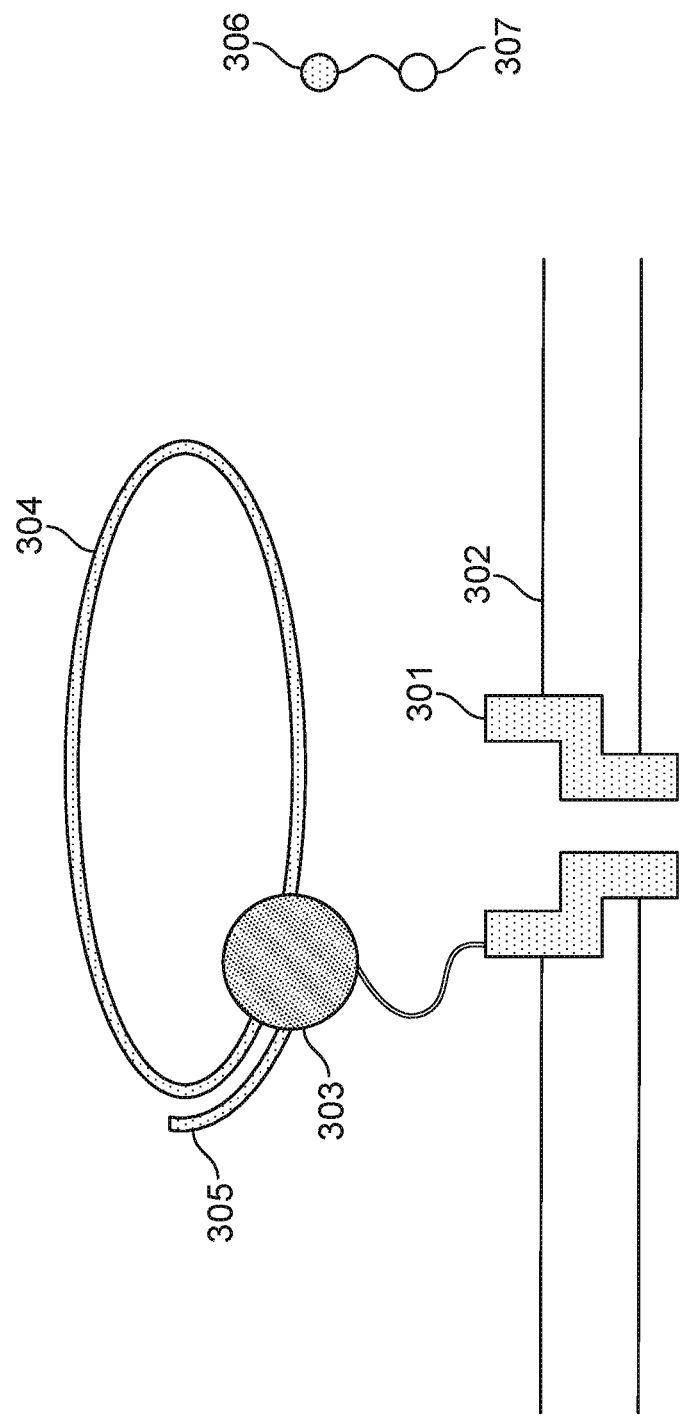
FIG. 3 illustrates an embodiment of a cell about to perform nucleotide sequencing with pre-loaded tags.

FIG. 3 illustrates an embodiment of a cell about to perform nucleotide sequencing with pre-loaded tags. A nanopore 301 is formed in a membrane 302. An enzyme 303 (e.g., a polymerase, such as a DNA polymerase) is associated with the nanopore. In some cases, polymerase 303 is covalently attached to nanopore 301. Polymerase 303 is associated with a nucleic acid molecule 304 to be sequenced. In some embodiments, the nucleic acid molecule 304 is circular. In some cases, nucleic acid molecule 304 is linear. In some embodiments, a nucleic acid primer 305 is hybridized to a portion of nucleic acid molecule 304. Polymerase 303 catalyzes the incorporation of nucleotides 306 onto primer 305 using single stranded nucleic acid molecule 304 as a template. Nucleotides 306 comprise tag species ("tags") 307.

Figure 4:
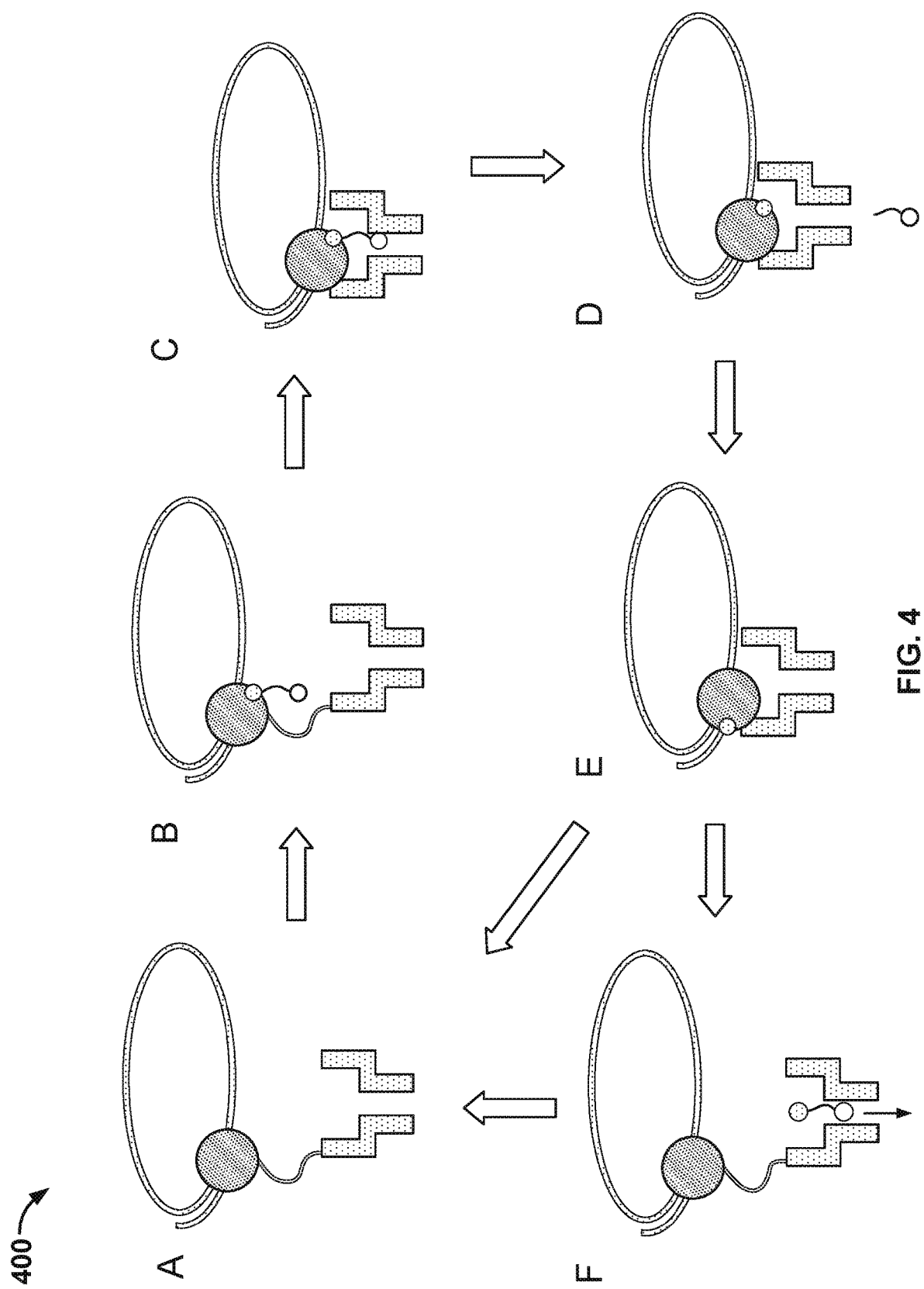
FIG. 4 illustrates an embodiment of a process 400 for nucleic acid sequencing with pre-loaded tags.

FIG. 4 illustrates an embodiment of a process 400 for nucleic acid sequencing with pre-loaded tags. Stage A illustrates the components as described in FIG. 3. Stage C shows the tag loaded into the nanopore. A "loaded" tag may be one that is positioned in and/or remains in or near the nanopore for an appreciable amount of time, e.g., 0.1 millisecond (ms) to 10,000 ms. In some cases, a tag that is pre-loaded is loaded in the nanopore prior to being released from the nucleotide. In some instances, a tag is pre-loaded if the probability of the tag passing through (and/or being detected by) the nanopore after being released upon a nucleotide incorporation event is suitably high, e.g., 90% to 99%.

At stage A, a tagged nucleotide (one of four different types: A, T, G, or C) is not associated with the polymerase. At stage B, a tagged nucleotide is associated with the polymerase. At stage C, the polymerase is docked to the nanopore. The tag is pulled into the nanopore during docking by an electrical force, such as a force generated in the presence of an electric field generated by a voltage applied across the membrane and/or the nanopore.

Some of the associated tagged nucleotides are not base paired with the nucleic acid molecule. These non-paired nucleotides typically are rejected by the polymerase within a time scale that is shorter than the time scale for which correctly paired nucleotides remain associated with the polymerase. Since the non-paired nucleotides are only transiently associated with the polymerase, process 400 as shown in FIG. 4 typically does not proceed beyond stage D. For example, a non-paired nucleotide is rejected by the polymerase at stage B or shortly after the process enters stage C.

Before the polymerase is docked to the nanopore, the conductance of the nanopore is ~300 picosiemens (300 pS). At stage C, the conductance of the nanopore is about 60 pS, 80 pS, 100 pS, or 120 pS, corresponding to one of the four types of tagged nucleotides respectively. The polymerase undergoes an isomerization and a transphosphorylation reaction to incorporate the nucleotide into the growing nucleic acid molecule and release the tag molecule. In particular, as the tag is held in the nanopore, a unique conductance signal (e.g., see signal 210 in FIG. 2) is generated due to the tag's distinct chemical structures, thereby identifying the added base electronically. Repeating the cycle (i.e., stage A through E or stage A through F) allows for the sequencing of the nucleic acid molecule. At stage D, the released tag passes through the nanopore.

In some cases, tagged nucleotides that are not incorporated into the growing nucleic acid molecule will also pass through the nanopore, as seen in stage F of FIG. 4. The unincorporated nucleotide can be detected by the nanopore in some instances, but the method provides a means for distinguishing between an incorporated nucleotide and an unincorporated nucleotide based at least in part on the time for which the nucleotide is detected in the nanopore. Tags bound to unincorporated nucleotides pass through the nanopore quickly and are detected for a short period of time (e.g., less than 10 ms), while tags bound to incorporated nucleotides are loaded into the nanopore and detected for a long period of time (e.g., at least 10 ms).

Figure 5:
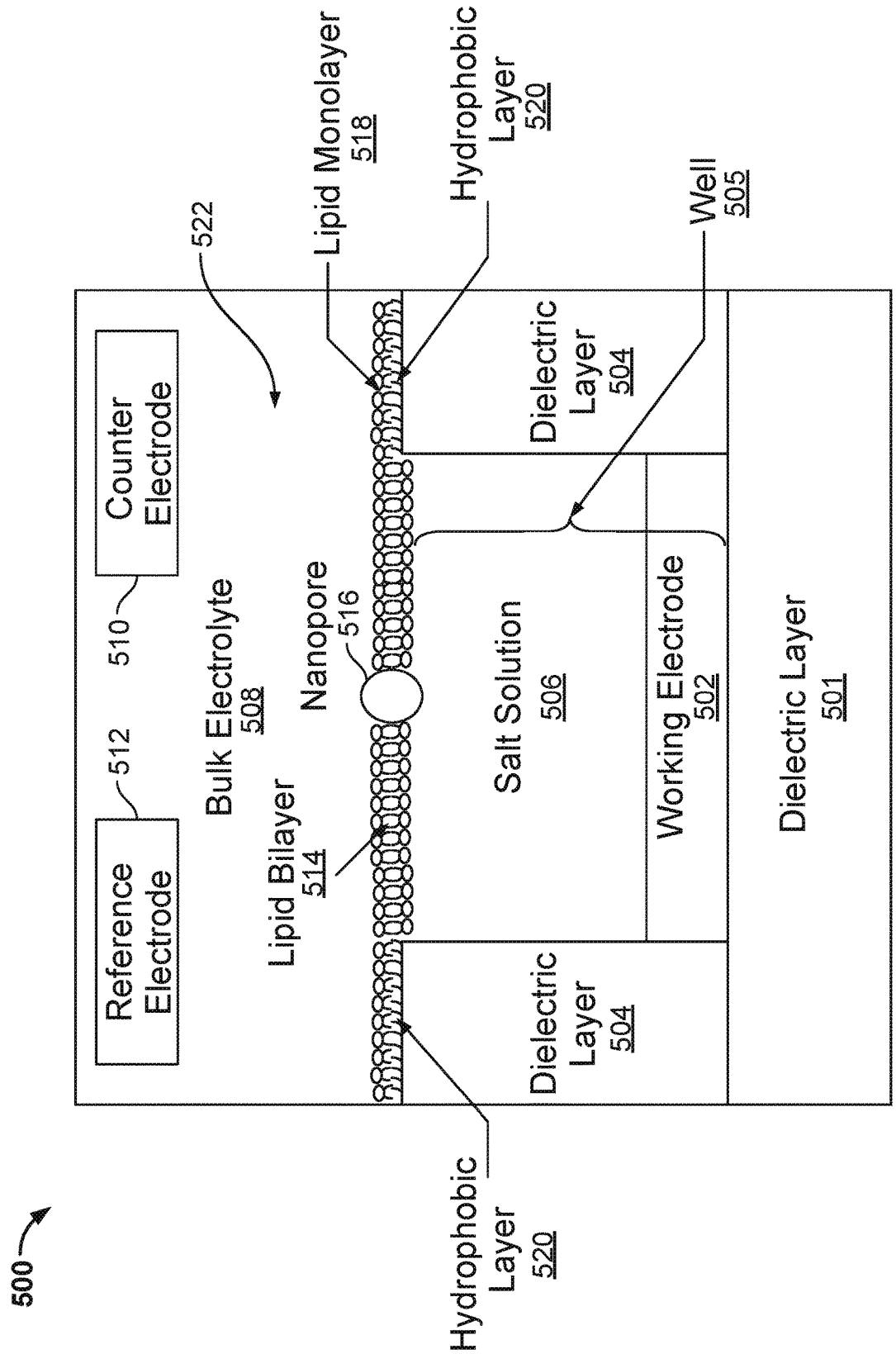
FIG. 5 illustrates an embodiment of a cell 500 in a nanopore based sequencing chip.

FIG. 5 illustrates an embodiment of a cell 500 in a nanopore based sequencing chip. Cell 500 includes a well 505 having two side walls and a bottom. In one embodiment, each side wall comprises a dielectric layer 504 and the bottom comprises a working electrode 502. In one embodiment, the working electrode 502 has a top side and a bottom side. In another embodiment, the top side of 502 makes up the bottom of the well 505 while the bottom side of 502 is in contact with dielectric layer 501. In another embodiment, the dielectric layer 504 is above dielectric layer 501. Dielectric layer 504 forms the walls surrounding a well 505 in which a working electrode 502 is located at the bottom. Suitable dielectric materials for use in the present invention (e.g., dielectric layer 501 or 504) include, without limitation, porcelain (ceramic), glass, mica, plastics, oxides, nitrides (e.g., silicon mononitride or SiN), silicon oxynitride, metal oxides, metal nitrides, metal silicates, transition-metal oxides, transition-metal nitrides, transition metal-silicates, oxynitrides of metals, metal aluminates, zirconium silicate, zirconium aluminate, hafnium oxide, insulating materials (e.g., polymers, epoxies, photoresist, and the like), or combinations thereof. Those of ordinary skill in the art will appreciate other dielectric materials that are suitable for use in the present invention.

In one aspect, cell 500 also includes one or more hydrophobic layers. As shown in FIG. 5, each dielectric layer 504 has a top surface. In one embodiment, the top surface of each dielectric layer 504 may comprise a hydrophobic layer. In one embodiment, silanization forms a hydrophobic layer 520 above the top surface of dielectric layer 504. For example, further silanization with silane molecules (i) containing 6 to 20 carbon-long chains (e.g., octadecyl-trichlorosilane, octadecyl-trimethoxysilane, or octadecyl-triethoxysilane), (ii) dimethyloctylchlorosilane (DMOC), or (iii) organofunctional alkoxysilane molecules (e.g., dimethylchloro-octodecyl-silane, methyldichloro-octodecyl-silane, trichloro-octodecyl-silane, trimethyl-octodecyl-silane, or triethyl-octodecyl-silane) can be done on the top surface of dielectric layer 504. In one embodiment, the hydrophobic layer is a silanized layer or silane layer. In one embodiment, the silane layer can be one molecule in thickness. In one aspect, dielectric layer 504 comprises a top surface suitable for adhesion of a membrane (e.g., a lipid bilayer comprising a nanopore). In one embodiment, the top surface suitable for adhesion of a membrane comprises a silane molecule as described herein. In some embodiments, hydrophobic layer 520 has a thickness provided in a nanometer (nM) or micrometer (µm) scale. In other embodiments, the hydrophobic layer may extend down along all or a part of the dielectric layer 504. (see also Davis et al. U.S. 20140034497, which is incorporated herein by reference in its entirety).

In another aspect, well 505 (formed by the dielectric layer walls 504) further includes a volume of salt solution 506 above working electrode 502. In general, the methods of the present invention comprise the use of a solution (e.g., a salt solution, salt buffer solution, electrolyte, electrolyte solution, or bulk electrolyte) that comprises osmolytes. As used herein, the term "osmolyte" refers to any soluble compound that when dissolved into solution increases the osmolarity of that solution. In the present invention, an osmolyte is a compound that is soluble in solution within the architecture of a nanopore sequencing system, e.g., a well containing a salt solution or a bulk electrolyte as described herein. As such, the osmolytes of the present invention affect osmosis, particularly osmosis across a lipid bilayer. Osmolytes for use in the present invention include, without limitation, ionic salts such as lithium chloride (LiCl), sodium chloride (NaCl), potassium chloride (KCl), lithium glutamate, sodium glutamate, potassium glutamate, lithium acetate, sodium acetate, potassium acetate, calcium chloride ($CaCl_2$), strontium chloride ($SrCl_2$), manganese chloride ($MnCl_2$), and magnesium chloride ($MgCl_2$); polyols and sugars such as glycerol, erythritol, arabitol, sorbitol, mannitol, xylitol, mannisidomannitol, glycosyl glycerol, glucose, fructose, sucrose, trehalose, and isofluoroside; polymers such as dextrans, levans, and polyethylene glycol; and some amino acids and derivatives thereof such as glycine, alanine, alpha-alanine, arginine, proline, taurine, betaine, octopine, glutamate, sarcosine, y-aminobutyric acid, and trimethylamine N-oxide ("TMAO") (see also e.g., Fisher et al. U.S. 20110053795, incorporated herein by reference in its entirety). In one embodiment, the present invention utilizes a solution comprising an osmolyte, wherein the osmolyte is an ionic salt. Those of ordinary skill in the art will appreciate other compounds that are suitable osmolytes for use in the present invention. In another aspect, the present invention provides solutions comprising two or more different osmolytes.

The architecture of the nanopore based sequencing chip described herein comprises an array of wells (e.g., FIG. 5) having a volume of between 1 attoliter and 1 nanoliter.

As shown in FIG. 5, a membrane is formed on the top surfaces of dielectric layer 504 and spans across well 505. For example, the membrane includes a lipid monolayer 518 formed on top of hydrophobic layer 520. As the membrane reaches the opening of well 505, the lipid monolayer transitions to a lipid bilayer 514 that spans across the opening of the well. The lipid monolayer 518 may also extend along all or a part of the vertical surface (i.e., side wall) of a dielectric layer 504. In one embodiment, the vertical surface 504 along which the monolayer 518 extends comprises a hydrophobic layer. A bulk electrolyte 508 containing protein nanopore transmembrane molecular complexes (PNTMC) and the analyte of interest is placed directly above the well. A single PNTMC/nanopore 516 is inserted into lipid bilayer 514. In one embodiment, insertion into the bilayer is by electroporation. Nanopore 516 crosses lipid bilayer 514 and provides the only path for ionic flow from bulk electrolyte 508 to working electrode 502.

Cell 500 includes a counter electrode (CE) 510, which is in electrical contact with the bulk electrolyte 508. Cell 500 may optionally include a reference electrode 512. In some embodiments, counter electrode 510 is shared between a plurality of cells, and is therefore also referred to as a common electrode. The common electrode can be configured to apply a common potential to the bulk liquid in contact with the nanopores in the measurements cells. The common potential and the common electrode are common to all of the measurement cells.

In some embodiments, working electrode 502 is a metal electrode. For non-faradaic conduction, working electrode 502 may be made of metals that are resistant to corrosion and oxidation, e.g., platinum, gold, titanium nitride and graphite. For example, working electrode 502 may be a platinum electrode with electroplated platinum. In another example, working electrode 502 may be a titanium nitride (TiN) working electrode.

As shown in FIG. 5, nanopore 516 is inserted into the planar lipid bilayer 514 suspended over well 505. An electrolyte solution is present both inside well 505, i.e., trans side, (see salt solution 506) and in a much larger external reservoir 522, i.e., cis side, (see bulk electrolyte 508). The bulk electrolyte 508 in external reservoir 522 is above multiple wells of the nanopore based sequencing chip. Lipid bilayer 514 extends over well 505 and transitions to lipid monolayer 518 where the monolayer is attached to hydrophobic layer 520. This geometry both electrically and physically seals well 505 and separates the well from the larger external reservoir. While neutral molecules, such as water and dissolved gases, may pass through lipid bilayer 514, ions may not. Nanopore 516 in lipid bilayer 514 provides a single path for ions to be conducted into and out of well 505.

For nucleic acid sequencing, a polymerase is attached to nanopore 516. A template of nucleic acid (e.g., DNA) is held by the polymerase. For example, the polymerase synthesizes DNA by incorporating hexaphosphate mono-nucleotides (HMN) from solution that are complementary to the template. A unique, polymeric tag is attached to each HMN. During incorporation, the tag threads the nanopore aided by an electric field gradient produced by the voltage between counter electrode 510 and working electrode 502. The tag partially blocks nanopore 516, procuring a measurable change in the ionic current through nanopore 516. In some embodiments, an alternating current (AC) bias or direct current (DC) voltage is applied between the electrodes.

Figure 6:
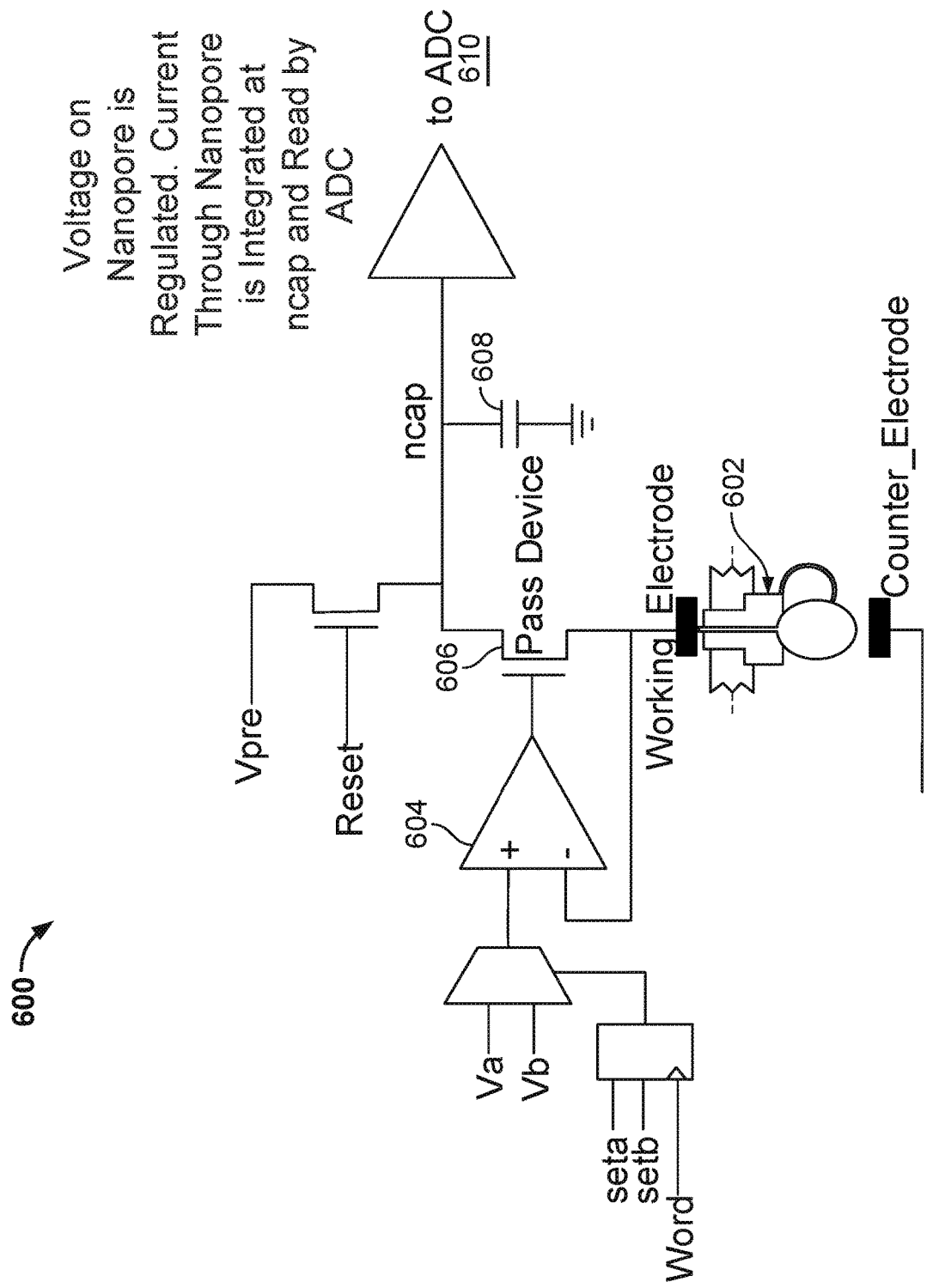
FIG. 6 illustrates an embodiment of a circuitry 600 in a cell of a nanopore based sequencing chip.

FIG. 6 illustrates an embodiment of a circuitry 600 in a cell of a nanopore based sequencing chip. As mentioned above, when the tag is held in nanopore 602, a unique conductance signal (e.g., see signal 210 in FIG. 2) is generated due to the tag's distinct chemical structures, thereby identifying the added base electronically. The circuitry in FIG. 6 maintains a constant voltage across nanopore 602 when the current flow is measured. In particular, the circuitry includes an operational amplifier 604 and a pass device 606 that maintain a constant voltage equal to $V_a$ or $V_b$ across nanopore 602. The current flowing through nanopore 602 is integrated at a capacitor $n_{cap}$ 608 and measured by an Analog-to-Digital (ADC) converter 610.

However, circuitry 600 has a number of drawbacks. One of the drawbacks is that circuitry 600 only measures unidirectional current flow. Another drawback is that operational amplifier 604 in circuitry 600 may introduce a number of performance issues. For example, the offset voltage and the temperature drift of operational amplifier 604 may cause the actual voltage applied across nanopore 602 to vary across different cells. The actual voltage applied across nanopore 602 may drift by tens of millivolts above or below the desired value, thereby causing significant measurement inaccuracies. In addition, the operational amplifier noise may cause additional detection errors. Another drawback is that the portions of the circuitry for maintaining a constant voltage across the nanopore while current flow measurements are made are area-intensive. For example, operational amplifier 604 occupies significantly more space in a cell than other components. As the nanopore based sequencing chip is scaled to include more and more cells, the area occupied by the operational amplifiers may increase to an unattainable size. Unfortunately, shrinking the operational amplifier's size in a nanopore based sequencing chip with a large-sized array may raise other performance issues; for example, it may exacerbate the offset and noise problems in the cells even further. Therefore, an improved circuitry and an improved method to analyze molecules using nanopores would be desirable.

Figure 7A:
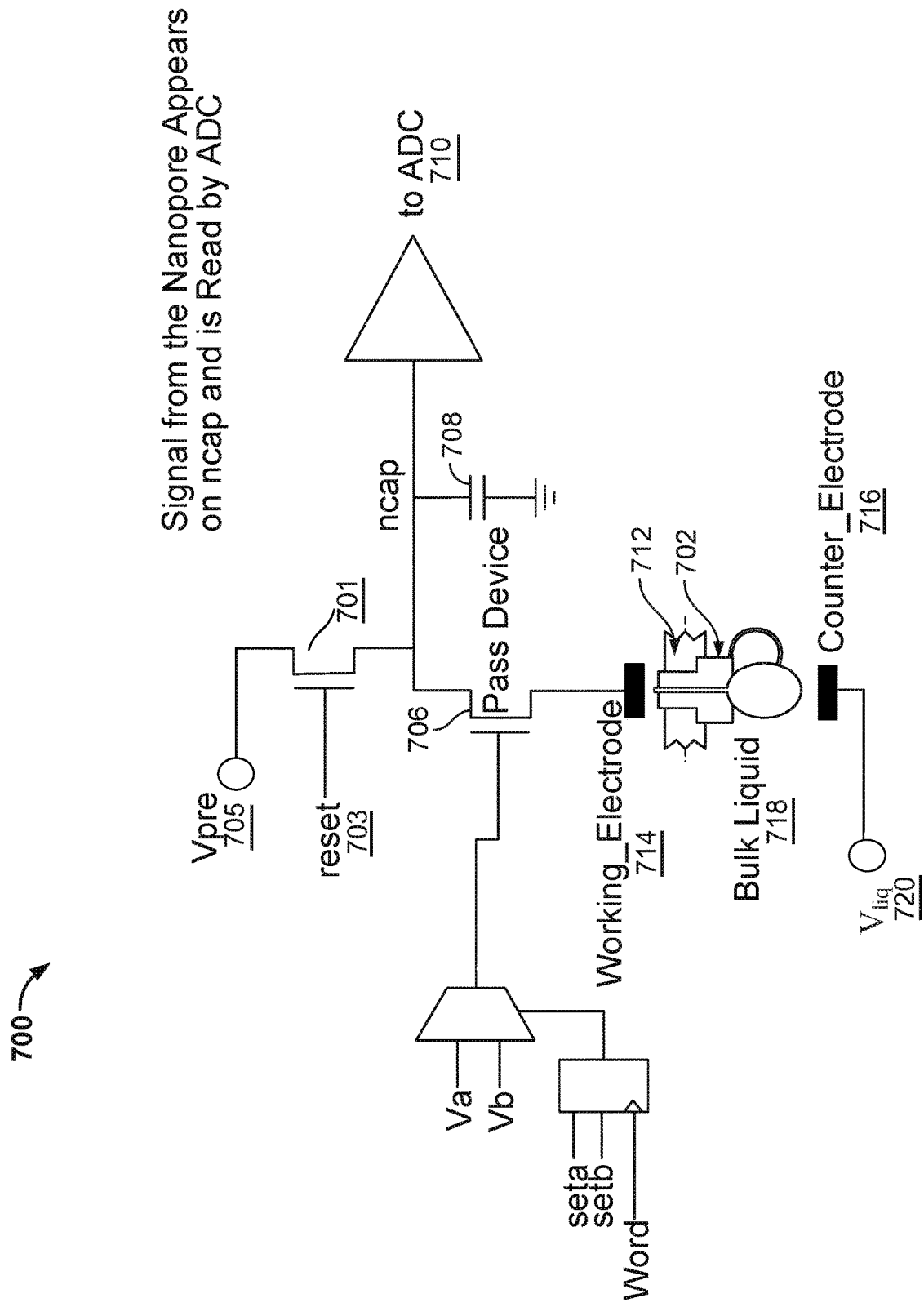
FIG. 7A illustrates an embodiment of a circuitry 700 in a cell of a nanopore based sequencing chip, wherein the voltage applied across the nanopore can be configured to vary over a time period during which the nanopore is in a particular detectable state.

FIG. 7A illustrates an embodiment of a circuitry 700 in a cell of a nanopore based sequencing chip, wherein the voltage applied across the nanopore can be configured to vary over a time period during which the nanopore is in a particular detectable state. One of the possible states of the nanopore is an open-channel state, in which a tag-attached polyphosphate is absent from the barrel of the nanopore. Another four possible states of the nanopore correspond to the states when the four different types of tag-attached polyphosphate (A, T, G, or C) are held in the barrel of the nanopore. Yet another possible state of the nanopore is when the membrane is ruptured. In circuitry 700, the operational amplifier is no longer required.

FIG. 7A shows a nanopore 702 that is inserted into a membrane 712, and nanopore 702 and membrane 712 are situated between a cell working electrode 714 and a counter electrode 716, such that a voltage is applied across nanopore 702. Nanopore 702 is also in contact with a bulk liquid/electrolyte 718. Note that working electrode 714, nanopore 702, membrane 712, and counter electrode 716 are drawn upside down as compared to the working electrode, nanopore, membrane, and counter electrode in FIG. 1. Hereinafter, a cell is meant to include at least a membrane, a nanopore, a working cell electrode, and the associated circuitry. In some embodiments, the counter electrode is shared between a plurality of cells, and is therefore also referred to as a common electrode. The common electrode can be configured to apply a common potential to the bulk liquid in contact with the nanopores in the measurements cells by connecting the common electrode to a voltage source $V_{liq}$ 720. The common potential and the common electrode are common to all of the measurement cells. There is a working cell electrode within each measurement cell; in contrast to the common electrode, working cell electrode 714 is configurable to apply a distinct potential that is independent from the working cell electrodes in other measurement cells.

Figure 7B:
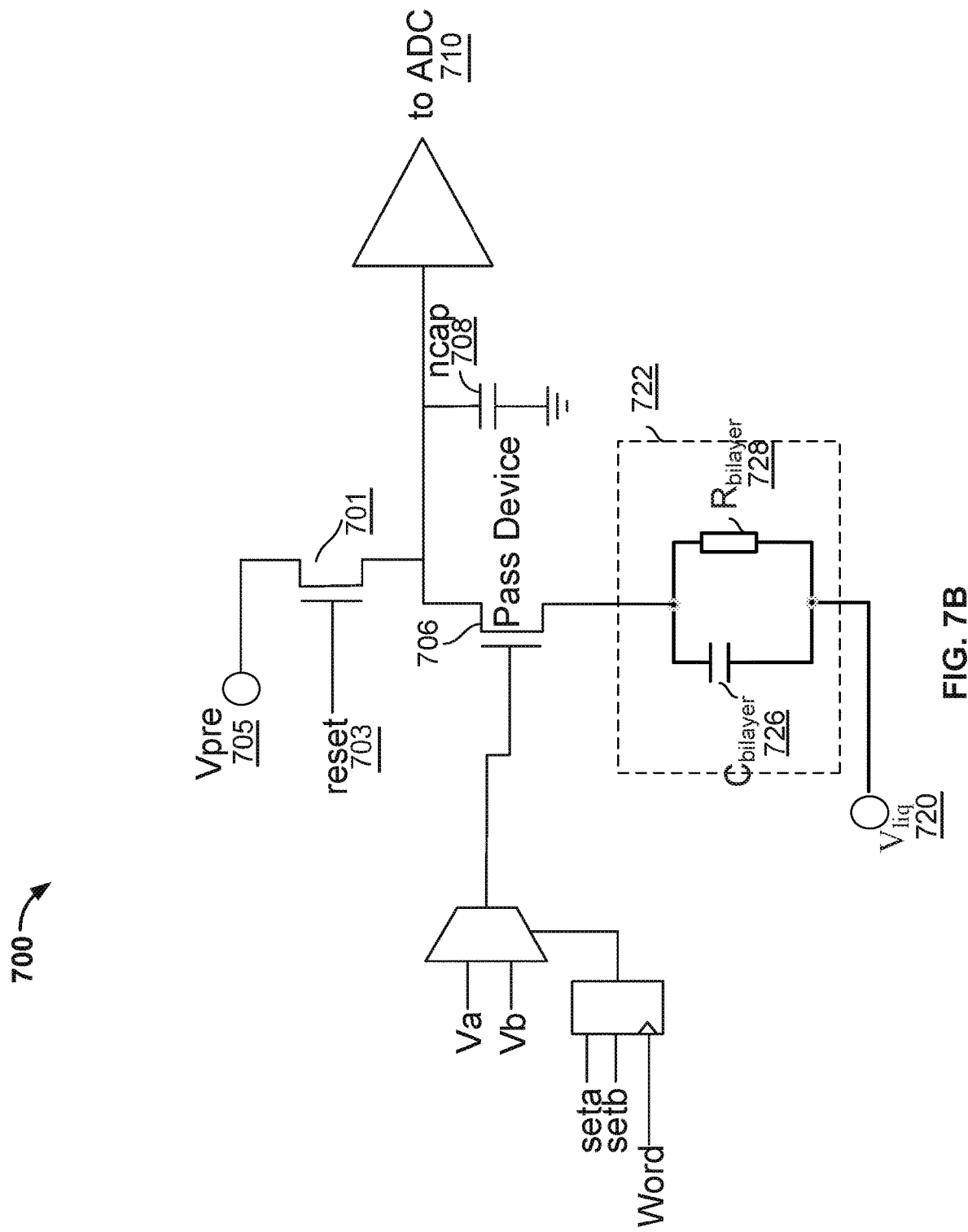
FIG. 7B illustrates an additional embodiment of a circuitry 700 in a cell of a nanopore based sequencing chip, wherein the voltage applied across the nanopore can be configured to vary over a time period during which the nanopore is in a particular detectable state.

FIG. 7B illustrates the same circuitry 700 in a cell of a nanopore based sequencing chip as that shown in FIG. 7A. Comparing to FIG. 7A, instead of showing a nanopore inserted in a membrane between the working electrode and the counter electrode, an electrical model 722 representing the electrical properties of the nanopore and membrane is shown.

Electrical model 722 includes a capacitor 726 ($C_{bilayer}$) that models a capacitance associated with the lipid bilayer and a resistor 728 ($R_{bilayer}$) that models a resistance associated with the nanopore/lipid bilayer in different states (e.g., the open-channel state or the states corresponding to having different types of tag/molecule inside the nanopore).

Voltage source $V_{liq}$ 720 is an alternating current (AC) voltage source. Counter electrode 716 is immersed in the bulk liquid 718, and an AC non-Faradaic mode is utilized to modulate a square wave voltage $V_{liq}$ and apply it to the bulk liquid in contact with the lipid membranes/bilayers in the measurement cells. In some embodiments, $V_{liq}$ is a square wave with a peak-to-peak magnitude variation of 100-250 mV and a frequency between 20 and 400 Hz.

Pass device 706 is a switch that can be used to connect or disconnect the lipid membrane/bilayer and the electrodes from the measurement circuitry 700. The switch enables or disables a voltage stimulus that can be applied across the lipid membrane/bilayer in the cell. Before lipids are deposited to the cell to form a lipid bilayer, the impedance between the two electrodes is very low because the well of the cell is not sealed, and therefore switch 706 is kept open to avoid a short-circuit condition. Switch 706 may be closed once lipid solvent has been deposited to the cell that seals the well of the cell.

Circuitry 700 further includes an on-chip fabricated integrating capacitor 708 ($n_{cap}$). Integrating capacitor 708 is pre-charged by using a reset signal 703 to close switch 701, such that integrating capacitor 708 is connected to a voltage source $V_{pre}$ 705. In some embodiments, voltage source $V_{pre}$ 705 provides a constant positive voltage with a magnitude of 900 mV. When switch 701 is closed, integrating capacitor 708 is pre-charged to the positive voltage level of voltage source $V_{pre}$ 705.

After integrating capacitor 708 is pre-charged, reset signal 703 is used to open switch 701 such that integrating capacitor 708 is disconnected from voltage source $V_{pre}$ 705. At this point, depending on the level of $V_{liq}$, the potential of counter electrode 716 may be at a higher level than the potential of working electrode 714, or vice versa. For example, during the positive phase of square wave $V_{liq}$ (i.e., the dark period of the AC voltage source signal cycle), the potential of counter electrode 716 is at a higher level than the potential of working electrode 714. Similarly, during the negative phase of square wave $V_{liq}$ (i.e., the bright period of the AC voltage source signal cycle), the potential of counter electrode 716 is at a lower level than the potential of working electrode 714. Due to this potential difference, integrating capacitor 708 may be charged during the dark period of the AC voltage source signal cycle and discharged during the bright period of the AC voltage source signal cycle. The charging or discharging causes an ionic current to flow through the nanopore.

Integrating capacitor 708 charges or discharges during a time period when switch 701 is opened by reset signal 703, and at the end of this time period, the voltage stored in integrating capacitor 708 may be read out by ADC 710. After the sampling by ADC 710, integrating capacitor 708 may be pre-charged again by using reset signal 703 to close switch 701, such that integrating capacitor 708 is connected to voltage source $V_{pre}$ 705 again. In some embodiments, the sampling rate of ADC 710 is between 500 to 2000 Hz. In some embodiments, the sampling rate of ADC 710 is up to 5 kHz. For example, with a sampling rate of 1 kHz, integrating capacitor 708 may be charged or discharged for a period of ~1 ms, and then the voltage at integrating capacitor 708 is read out by ADC 710. After the sampling by ADC 710, integrating capacitor 708 is pre-charged again by using reset signal 703 to close switch 701 such that integrating capacitor 708 is connected to voltage source $V_{pre}$ 705 again. The steps of pre-charging the integrating capacitor 708, waiting a fixed period of time for the integrating capacitor 708 to charge or discharge, and sampling the voltage stored in integrating capacitor by ADC 710 are then repeated in cycles. As will be described in greater detail below, the rate of voltage decay of the integrating capacitor caused by the charging and discharging of the capacitor may be monitored and used to analyze a molecule inside a nanopore.

Figure 8:
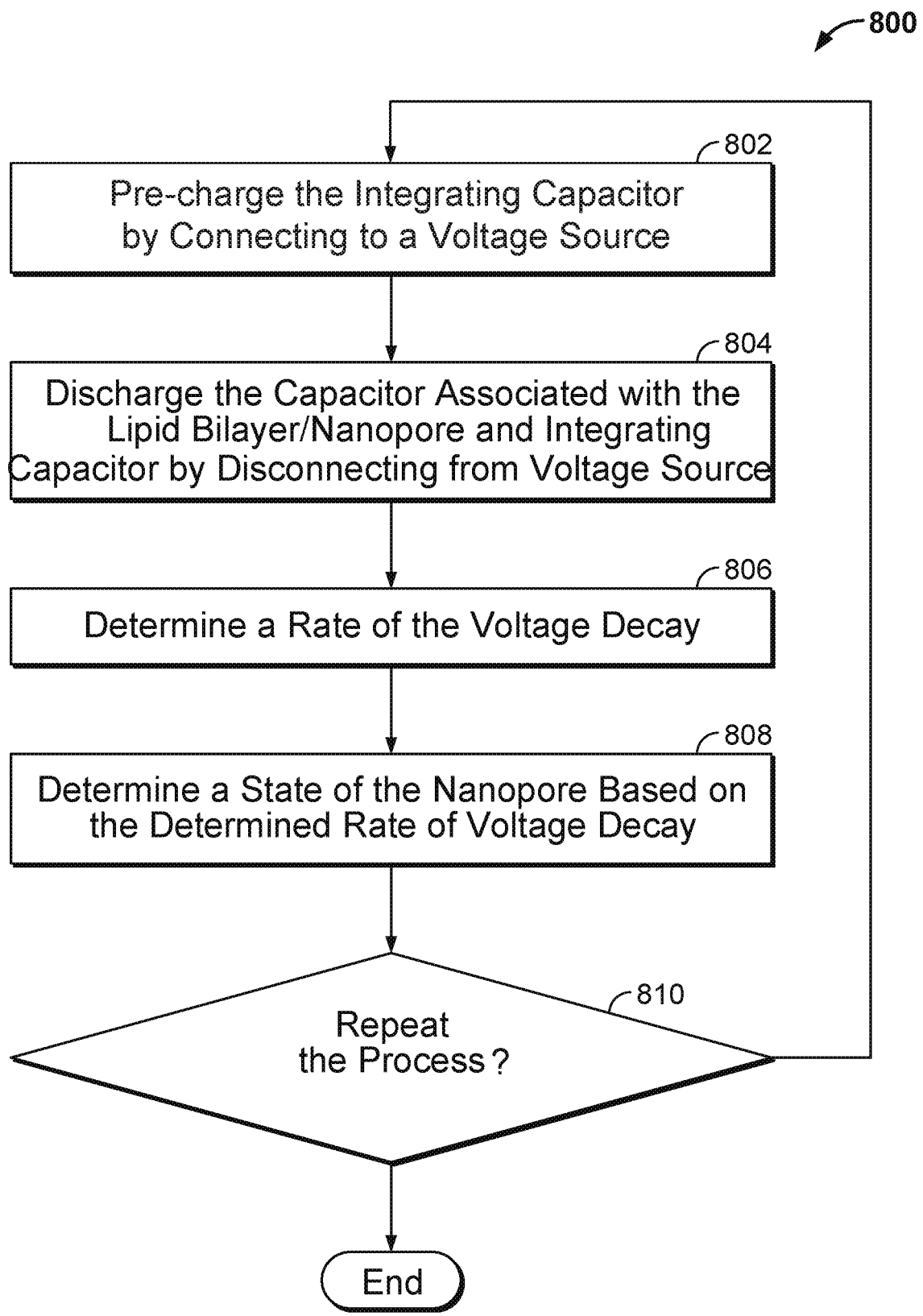
FIG. 8 illustrates an embodiment of a process 800 for analyzing a molecule inside a nanopore, wherein the nanopore is inserted in a membrane.
Figure 9:
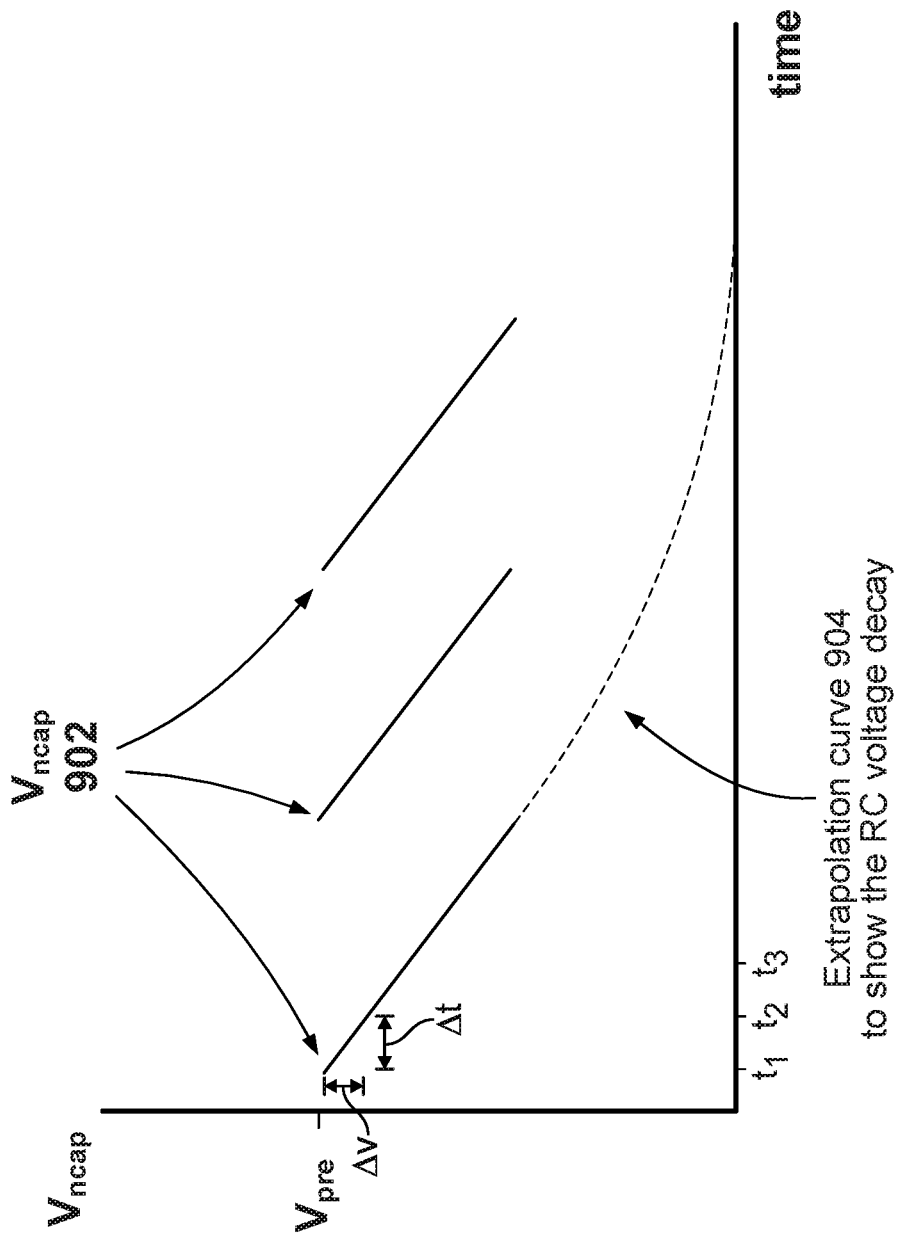
FIG. 9 illustrates an embodiment of a plot of the voltage at the integrating capacitor ($V_{ncap}$) versus time when process 800 is performed and repeated three times within a bright period of the AC voltage source signal cycle.

FIG. 8 illustrates an embodiment of a process 800 for analyzing a molecule inside a nanopore, wherein the nanopore is inserted in a membrane. Process 800 may be performed using the circuitries shown in FIGS. 7A and 7B. FIG. 9 illustrates an embodiment of a plot of the voltage at the integrating capacitor ($V_{ncap}$) versus time when process 800 is performed and repeated three times within a bright period of the AC voltage source signal cycle. Due to the discharging of the integrating capacitor, the voltage applied across the nanopore is not held constant. Instead, the voltage applied across the nanopore changes over time. The rate of the voltage decay (i.e., the steepness of the slope of the voltage at the integrating capacitor versus time plot) depends on the cell resistance (e.g., the resistance of resistor 728 in FIG. 7B). More particularly, as the resistance associated with the nanopore in different states (e.g., the open-channel state, the states corresponding to having different types of tag/molecule inside the nanopore, and the state when the membrane is ruptured) are different due to the molecules'/tags' distinct chemical structures, different corresponding rates of voltage decay may be observed and thus may be used to identify the different states of the nanopore.

With reference to FIG. 8 and FIG. 7B, at 802 of process 800, the integrating capacitor is pre-charged by coupling the integrating capacitor and the nanopore to a pre-charging voltage source. For example, as shown in FIG. 7B, integrating capacitor 708 is pre-charged to $V_{pre}$ by using a reset signal 703 to close switch 701, such that integrating capacitor 708 and the nanopore are coupled to a voltage source $V_{pre}$ 705. As shown in FIG. 9, the initial voltage at integrating capacitor is $V_{pre}$. As switch 701 is closed and the integrating capacitor is being pre-charged, the capacitor associated with the membrane is also charged simultaneously and energy is stored in an electric field across the membrane.

At 804 of process 800, the capacitor associated with the membrane (capacitor 726) and the integrating capacitor are discharged by decoupling the nanopore and the membrane from the voltage source, and the energy stored in the electric field across the membrane is thereby dissipated. For example, as shown in FIG. 7B, the voltage source $V_{pre}$ 705 is disconnected when switch 701 is opened by a reset signal 703. After switch 701 is opened, the voltage at the integrating capacitor begins to decay exponentially, as shown in FIG. 9. The exponential decay has a RC time constant $\tau=RC$, where R is the resistance associated with the nanopore (resistor 728) and C is the capacitance in parallel with R, including the capacitance associated with the membrane $C_{bilayer}$ 726 and the capacitance associated with $n_{cap}$ 708.

At 806 of process 800, a rate of decay of the voltage at the integrating capacitor is determined. The rate of voltage decay is the steepness of the slope of the voltage at the integrating capacitor versus time plot, as shown in FIG. 9. The rate of voltage decay may be determined in different ways.

In some embodiments, the rate of voltage decay is determined by measuring the voltage decay that occurs during a fixed time interval. For example, as shown in FIG. 9, the voltage at the integrating capacitor is first measured by ADC 710 at time $t_1$, and then the voltage is again measured by ADC 710 at time $t_2$. The voltage difference $\Delta V$ is greater when the slope of the $V_{ncap}$ voltage versus time curve is steeper, and the voltage difference $\Delta V$ is smaller when the slope of the voltage versus time curve is less steep. Thus, $\Delta V$ may be used as a metric for determining the rate of decay of the voltage at the integrating capacitor. In some embodiments, to increase the accuracy of the measurement of the rate of voltage decay, the voltage may be measured additional times at fixed intervals. For example, the voltage may be measured at times $t_3$, $t_4$, and so on, and the multiple measurements of $\Delta V$ during the multiple time intervals may be jointly used as a metric for determining the rate of decay of the voltage at the integrating capacitor. In some embodiments, correlated double sampling (CDS) may be used to increase the accuracy of the measurement of the rate of voltage decay.

In some embodiments, the rate of voltage decay is determined by measuring the time duration that is required for a selected amount of voltage decay. In some embodiments, the time required for the voltage to drop from a fixed voltage $V_1$ to a second fixed voltage $V_2$ may be measured. The time required is less when the slope of the voltage versus time curve is steeper, and the time required is greater when the slope of the voltage versus time curve is less steep. Thus, the measured time required may be used as a metric for determining the rate of decay of the voltage at the integrating capacitor.

At 808 of process 800, a state of the nanopore is determined based on the determined rate of voltage decay. One of the possible states of the nanopore is an open-channel state during which a tag-attached polyphosphate is absent from the barrel of the nanopore. Other possible states of the nanopore correspond to the states when different types of molecules are held in the barrel of the nanopore. For example, another four possible states of the nanopore correspond to the states when the four different types of tag-attached polyphosphate (A, T, G, or C) are held in the barrel of the nanopore. Yet another possible state of the nanopore is when the membrane is ruptured. The state of the nanopore can be determined based on the determined rate of voltage decay, because the rate of voltage decay depends on the cell resistance; i.e., the resistance of resistor 728 in FIG. 7B. More particularly, as the resistances associated with the nanopore in different states are different due to the molecules/tags' distinct chemical structures, different corresponding rates of voltage decay may be observed and thus may be used to identify the different states of the nanopore.

Figure 10:
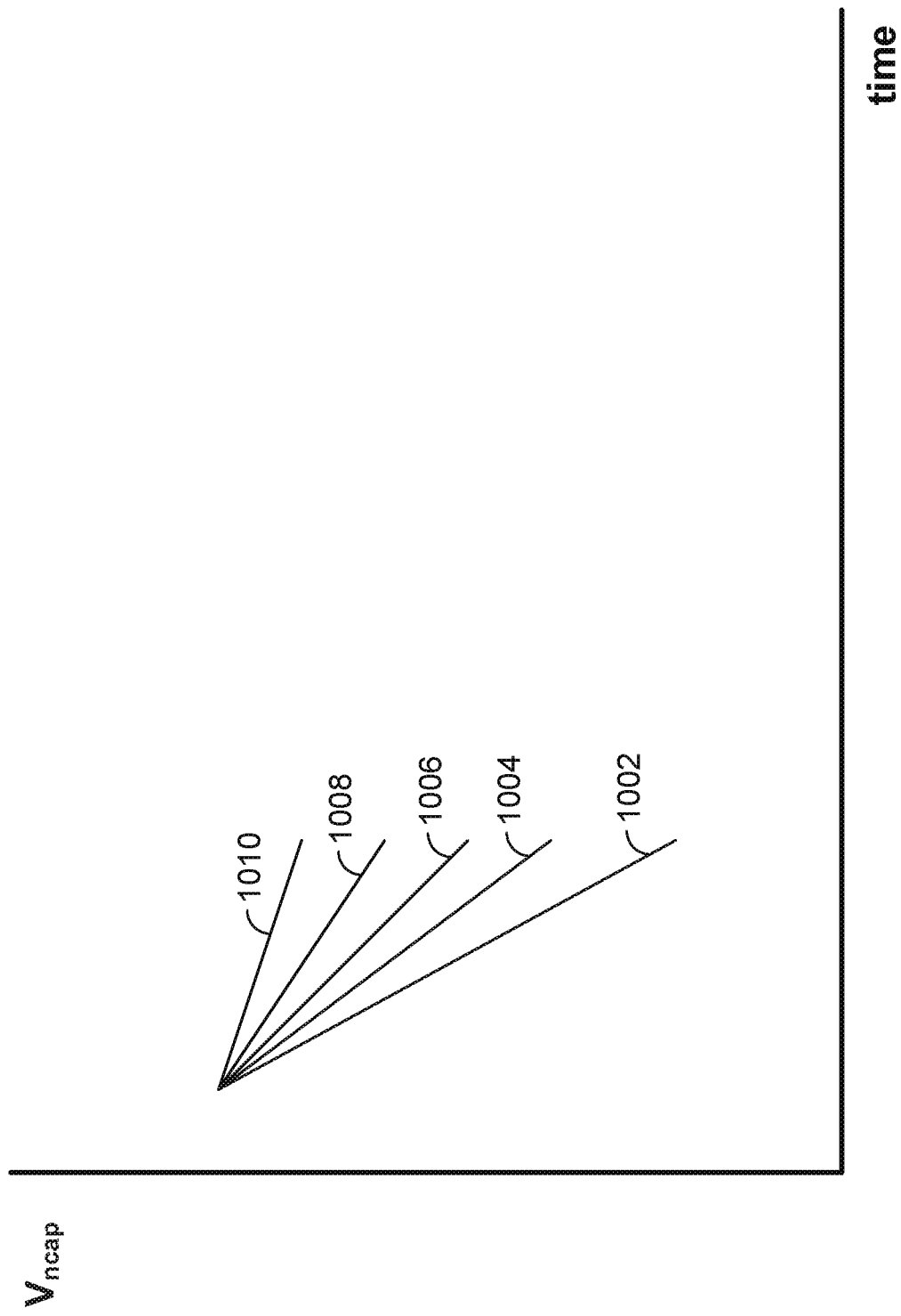
FIG. 10 illustrates an embodiment of the plots of the voltage at the integrating capacitor versus time when the nanopore is in different states.

FIG. 10 illustrates an embodiment of the plots of the voltage at the integrating capacitor versus time when the nanopore is in different states. Plot 1002 shows the rate of voltage decay during an open-channel state. In some embodiments, the resistance associated with the nanopore in an open-channel state is in the range of 100 Mohm to 20

Gohm. Plots 1004, 1006, 1008, and 1010 show the different rates of voltage decay corresponding to the four capture states when the four different types of tag-attached polyphosphate (A, T, G, or C) are held in the barrel of the nanopore. In some embodiments, the resistance associated with the nanopore in a capture state is within the range of 200 Mohm to 40 Gohm. Note that the slope of each of the plots is distinguishable from each other.

At 810 of process 800, it is determined whether process 800 is repeated. For example, the process may be repeated a plurality of times to detect each state of the nanopore. If the process is not repeated, then process 800 terminates; otherwise, the process restarts at 802 again. At 802, the integrating capacitor is pre-charged again by coupling the integrating capacitor and the nanopore to the pre-charging voltage source. For example, as shown in FIG. 7B, integrating capacitor 708 is pre-charged to $V_{pre}$ by using reset signal 703 to close switch 701, such that integrating capacitor 708 and the nanopore are coupled to a voltage source $V_{pre}$ 705. As shown in FIG. 9, the voltage at the integrating capacitor ($V_{ncap}$) jumps back up to the level of $V_{pre}$. As process 800 is repeated a plurality of times, a saw-tooth like voltage waveform is observed at the integrating capacitor over time. FIG. 9 also illustrates an extrapolation curve 904 showing the RC voltage decay over time had the voltage $V_{pre}$ 705 not been reasserted.

As shown above, configuring the voltage applied across the nanopore to vary over a time period during which the nanopore is in a particular detectable state has many advantages. One of the advantages is that the elimination of the operational amplifier that is otherwise fabricated on-chip in the cell circuitry significantly reduces the footprint of a single cell in the nanopore based sequencing chip, thereby facilitating the scaling of the nanopore based sequencing chip to include more and more cells (e.g., having millions of cells in a nanopore based sequencing chip).

Another advantage is that the circuitry of a cell does not suffer from offset inaccuracies because $V_{pre}$ is applied directly to the working electrode without any intervening circuitry. Another advantage is that since no switches are being opened or closed during the measurement intervals, the amount of charge injection is minimized.

Furthermore, the technique described above operates equally well using positive voltages or negative voltages. The voltage may be an alternating current (AC) voltage. Bidirectional measurements have been shown to be helpful in characterizing a molecular complex. In addition, bidirectional measurements are valuable when the type of ionic flow that is driven through the nanopore is via non-faradaic conduction. Two types of ionic flow can be driven through the nanopore: faradaic conduction and non-faradaic conduction. In faradaic conduction, a chemical reaction occurs at the surface of the metal electrode. The faradaic current is the current generated by the reduction or oxidation of some chemical substances at an electrode. The advantage of non-faradaic conduction is that no chemical reaction happens at the surface of the metal electrode.

Figure 11:
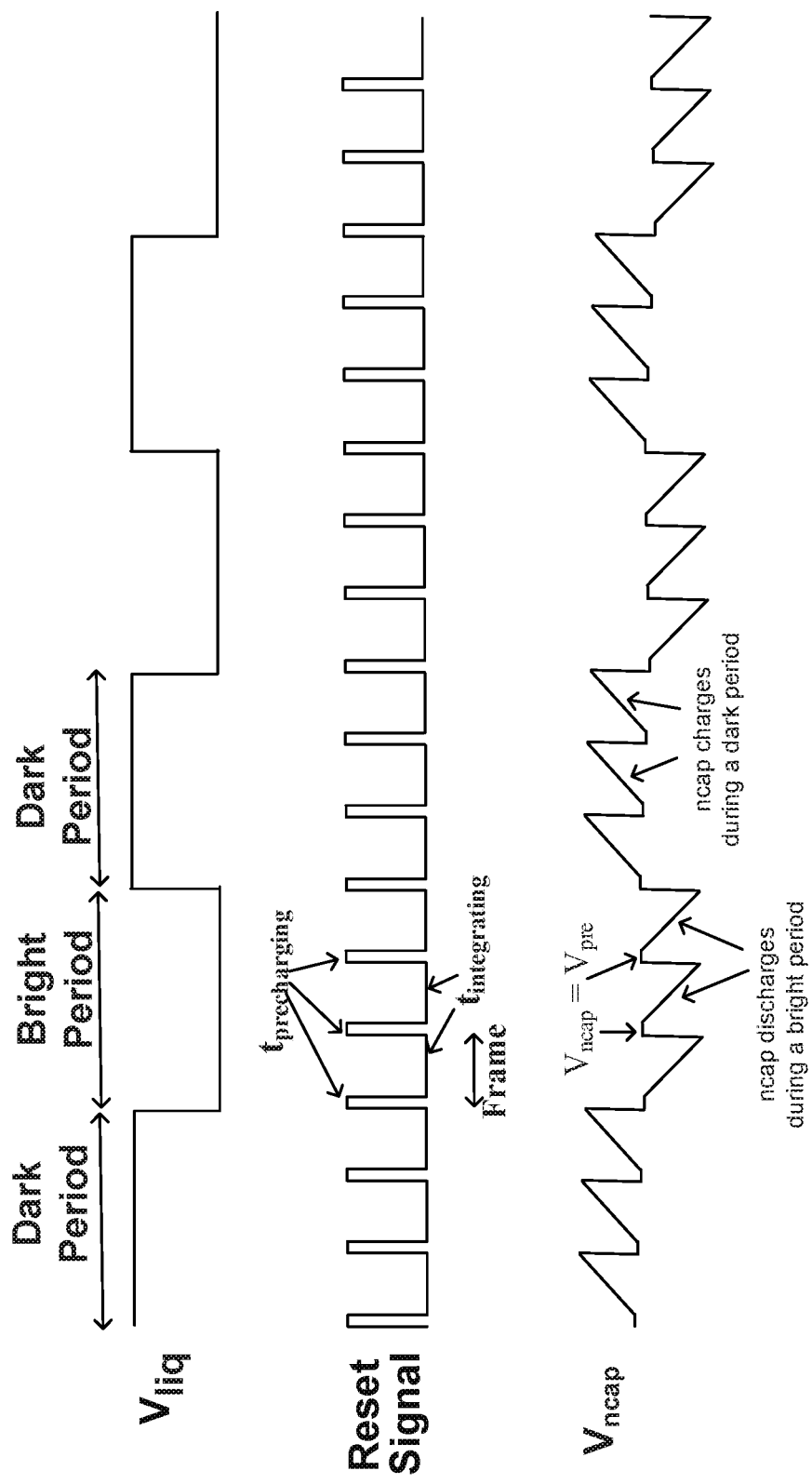
FIG. 11 illustrates an embodiment of a time signal plot of a plurality of signals in a cell of the nanopore based sequencing chip.

FIG. 11 illustrates an embodiment of a time signal plot of a plurality of signals in a cell of the nanopore based sequencing chip. In some embodiments, the signals are provided by the circuitries shown in FIGS. 7A and 7B. The topmost plot of $V_{liq}$ shows the voltage applied to common electrode 716 by voltage source $V_{liq}$ 720 over time. The middle plot shows a reset signal 703 that is used to control switch 701 versus time, wherein switch 701 connects or disconnects voltage source $V_{pre}$ 705 to or from the membrane in a cell of the nanopore based sequencing chip. The bottom plot shows the voltage at the integrating capacitor ($V_{ncap}$) in response to the reset signal and $V_{liq}$ as a function of time.

The topmost plot of $V_{liq}$ shows the voltage applied to the common electrode 716 by voltage source $V_{liq}$ 720 over time. Because common electrode 716 is immersed in bulk liquid 718, $V_{liq}$ is applied to the bulk liquid in contact with the lipid membranes/bilayers in the measurement cells. $V_{liq}$ is also referred to as the liquid voltage. In some embodiments, $V_{liq}$ is a square wave with a peak-to-peak magnitude variation of 200-250 mV and a frequency between 20 and 400 Hz (e.g., 40 Hz). For example, $V_{liq}$ may switch between the values of 0.8 V and 1.0 V. The time period when $V_{liq}$ is at the lower value (e.g., 0.8 V) is referred to as the bright period or tag-reading period, because it is the period when a tag may be pulled into the nanopore for analysis. The lower voltage value is also referred to as the tag-reading voltage. The time period when $V_{liq}$ is at the higher value (e.g., 1.0 V) is referred to as the dark period or open-channel period, because it is the period during which a tag-attached polyphosphate is repelled and absent from the barrel of the nanopore. The higher voltage value is also referred to as the open-channel voltage.

The middle plot shows a reset signal 703 that is used to control switch 701 versus time, wherein switch 701 connects or disconnects voltage source $V_{pre}$ 705 to or from the membrane (also $n_{cap}$ 708) in a cell of the nanopore based sequencing chip. When the reset signal is held at high during the time periods $t_{pre-charging}$, switch 701 is closed, and when the reset signal is held at low during the time periods $t_{integrating}$, switch 701 is open. One $t_{pre-charging}$ period combined with one $t_{integrating}$ period together form a single frame. In some embodiments, the frame rate is 2 kHz with a single frame duration of 500 μs. In other embodiments, the frame rate is within the range of 200 Hz to 15 kHz. For ease of illustration, only three frames of the reset signal are drawn within a single bright period of $V_{liq}$ in FIG. 11. However, it should be recognized that there may be tens or hundreds of frames within each bright period or dark period.

When switch 701 is closed during a time period $t_{pre-charging}$, voltage source $V_{pre}$ 705 is connected to working electrode 714, applying a voltage $V_{pre}$ to the cell working electrode, and the capacitor associated with the membrane ($C_{bilayer}$ 726) and integrating capacitor $n_{cap}$ 708 are pre-charged to the voltage $V_{pre}$. Accordingly, the voltage at the integrating capacitor, $V_{ncap}$ (see the bottom plot of FIG. 11), is equal to $V_{pre}$ within each time period $t_{pre-charging}$. In some embodiments, voltage source $V_{pre}$ 705 provides a constant positive voltage with a magnitude of 0.9 V. In other embodiments, $V_{pre}$ is a constant voltage selected from within a range of 0.7 to 1.2 V.

After the capacitors are pre-charged, switch 701 is opened by the low reset signal during a time period $t_{integrating}$, decoupling the nanopore, the membrane, and $n_{cap}$ 708 from voltage source $V_{pre}$ 705. During a time period $t_{integrating}$, the capacitors either discharge or charge, and $V_{ncap}$ either decays or increases exponentially, depending on the level of $V_{liq}$. When the time period $t_{integrating}$ falls within a bright period of $V_{liq}$, $V_{liq}$ is at a lower voltage level than $V_{ncap}$, and this potential difference causes the capacitors to discharge and $V_{ncap}$ to decay exponentially. When the time period $t_{integrating}$ falls within a dark period of $V_{liq}$, $V_{ncap}$ is at a lower voltage level than $V_{liq}$, and this potential difference causes the capacitors to charge up and $V_{ncap}$ to increase exponentially instead. The exponential voltage change has a RC time constant τ=RC, where R is the resistance associated with the nanopore ($R_{bilayer}$ 728) and C is the capacitance in parallel with R, including the capacitance associated with the membrane $C_{bilayer}$ 726 and the capacitance associated with $n_{cap}$ 708. It should be recognized that the steepness of the slope of $V_{ncap}$ is not drawn to scale in FIG. 11. The rate of the decay in $V_{ncap}$ caused by the discharging of the capacitors may vary from frame to frame, and the different rates of decay may be used to analyze a molecule inside a nanopore. The rate of the increase in $V_{ncap}$ caused by the charging of the capacitors may also vary from frame to frame, and the different rates of increase in $V_{ncap}$ may be monitored for calibrating the open-channel state, such as drift correction.

In the embodiment shown in FIG. 11, the reset signal is kept high for a brief (0.5 to 50 microseconds) $t_{pre\text{-}charging}$ period only, and as soon as the capacitors are pre-charged to $V_{pre}$, the reset signal is set to a low level to open the switch, allowing the voltage at integrating capacitor ncap 708 to float and change to a voltage other than $V_{pre}$. Quick transitions of the reset signal, especially the quick transitions of the reset signal when $V_{liq}$ switches from a dark period to a bright period or vice versa, have been found to create certain $V_{ncap}$ time profiles that may cause a number of performance issues in the nanopore based sequencing chip. For example, the quick transitions of the reset signal and the corresponding $V_{ncap}$ time profile may cause unpredictable transient characteristics in the lipid bilayer, affecting the measurement of the rate of change of $V_{ncap}$ during the integrating periods. The quick transitions of the reset signal also reduce the threading probability, i.e., the probability of a tag being captured in the barrel of a nanopore during the bright periods. Therefore, improved reset signal patterns and $V_{ncap}$ voltage patterns would be desirable.

Figure 12:
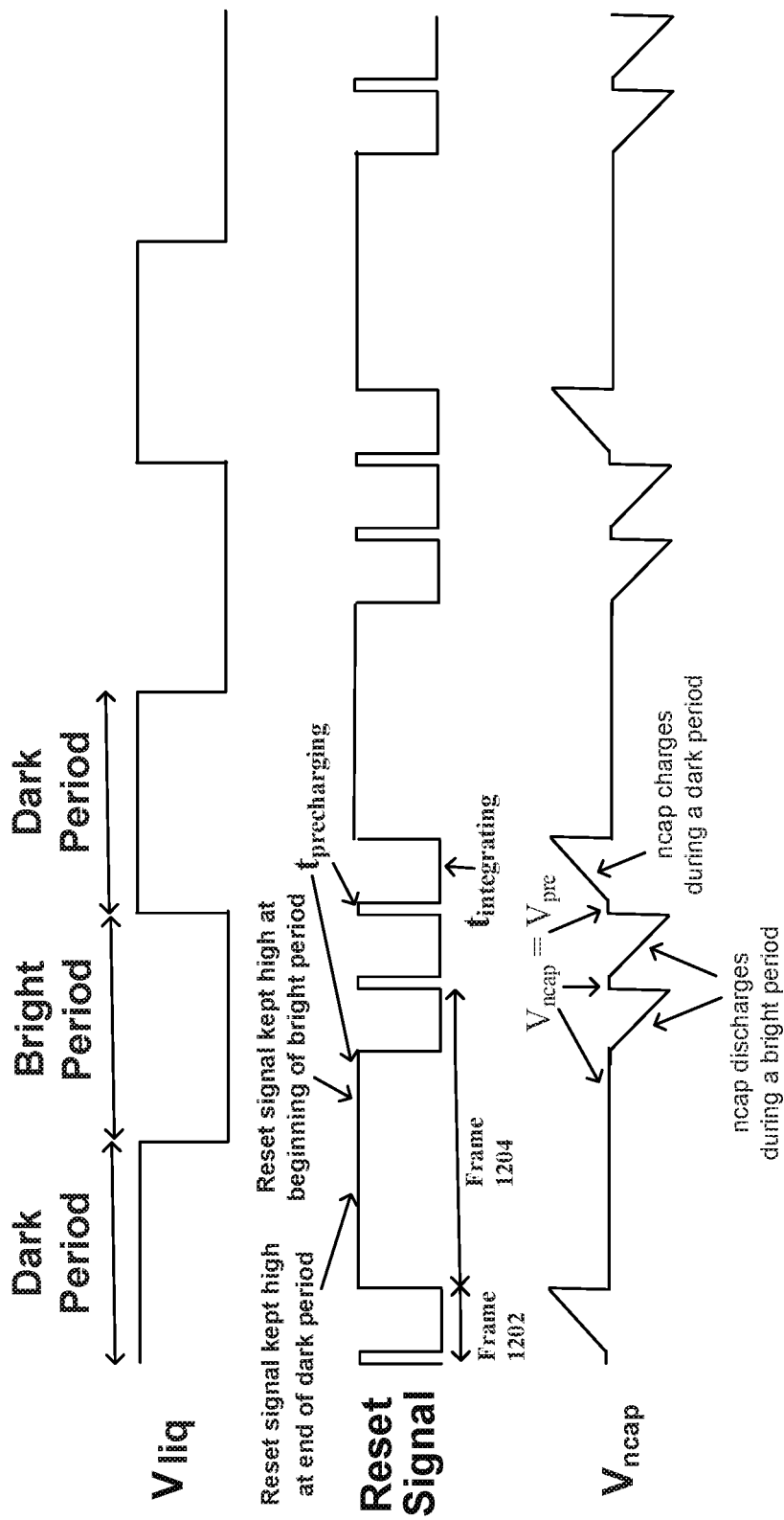
FIG. 12 illustrates another embodiment of a reset signal that is used to control the switch that connects or disconnects the voltage source to or from the membrane in a cell of the nanopore based sequencing chip.

FIG. 12 illustrates another embodiment of a reset signal that is used to control the switch that connects or disconnects the voltage source to or from the membrane in a cell of the nanopore based sequencing chip, such that the capacitor associated with the membrane is charged and discharged repeatedly. In some embodiments, the signals are provided by the circuitries shown in FIGS. 7A and 7B. The topmost plot $V_{liq}$ is identical to the $V_{liq}$ plot in FIG. 11. The middle plot shows an improved reset signal 703 that is used to control switch 701 versus time, wherein switch 701 connects or disconnects voltage source $V_{pre}$ 705 to or from the membrane in a cell of the nanopore based sequencing chip. The bottom plot shows the voltage at the integrating capacitor ($V_{ncap}$) in response to the new improved reset signal and $V_{liq}$ as a function of time.

The topmost plot $V_{liq}$ shows the voltage applied to the common electrode 716 by voltage source $V_{liq}$ 720 over time. In some embodiments, $V_{liq}$ is a square wave with a peak-to-peak magnitude variation of 200-250 mV and a frequency between 20 and 400 Hz (e.g., 40 Hz). For example, $V_{liq}$ may switch between the values of 0.8 V and 1.0 V. The time period when $V_{liq}$ is at the lower value (e.g., 0.8 V) is referred to as the bright period or tag-reading period. The time period when $V_{liq}$ is at the higher value (e.g., 1.0 V) is referred to as the dark period or open-channel period.

The middle plot shows an improved reset signal 703 that is used to control switch 701 versus time, wherein switch 701 connects or disconnects voltage source $V_{pre}$ 705 to or from the membrane (also $n_{cap}$ 708) in a cell of the nanopore based sequencing chip. When the reset signal is held at high during the time periods $t_{pre\text{-}charging}$, switch 701 is closed, and when the reset signal is held at low during the time periods $t_{integrating}$, switch 701 is open. One $t_{pre\text{-}charging}$ period followed by one $t_{integrating}$ period together form a single frame.

In contrast to the frames in FIG. 11, the duration of the frames in FIG. 12 are not kept constant over time. There are two types of frames in the reset signal. The different types of frames result in different $V_{ncap}$ patterns, and thus the corresponding improved techniques are referred to as the voltage mode with hybrid mode stimuli. One type of frame (see e.g., frame 1202) is similar to the frames in FIG. 11. In these frames, the reset signal is maintained at a high level for a very brief $t_{pre\text{-}charging}$ period only, and as soon as the capacitors are pre-charged to $V_{pre}$, the reset signal is set to a low level to open the switch, allowing the voltage at integrating capacitor ncap 708 to float and change to a voltage other than $V_{pre}$. A second type of frame (see e.g., frame 1204) has longer pre-charging periods than the first type of frames. As shown in frame 1204, the reset signal is kept at the high level for a longer $t_{pre\text{-}charging}$ period. In particular, the reset signal is maintained at the high level during the ending portion of a $V_{liq}$ dark period and the beginning portion of a $V_{liq}$ bright period, such that there are no quick transitions of the reset signal when $V_{liq}$ switches from a dark period to a bright period.

By extending the pre-charging period in frame 1204, voltage source $V_{pre}$ 705 is connected to working electrode 714 for a longer period, and the voltage at the integrating capacitor, $V_{ncap}$ (see the bottom plot of FIG. 12), is maintained at $V_{pre}$ when $V_{liq}$ switches from a dark period to a bright period. In some embodiments, voltage source $V_{pre}$ 705 provides a constant positive voltage with a magnitude of 0.9 V. In other embodiments, $V_{pre}$ is a constant voltage selected from within a range of 0.7 to 1.2 V.

Maintaining $V_{ncap}$ at a constant higher level when $V_{liq}$ switches from a dark period to a bright period has a number of advantages. One of the advantages is that it increases the threading probability, the probability of a tag being captured in the barrel of a nanopore during the bright periods. Maintaining $V_{ncap}$ at a constant higher voltage at the beginning portion of a $V_{liq}$ bright period increases the threading probability because the electrical force that can pull a tag into the nanopore remains high for a longer period of time, thereby increasing the chance that the tag is captured into the nanopore for measurement and decreasing the chance that a tag already trapped in the nanopore may escape from the nanopore. Another advantage of maintaining $V_{ncap}$ at a constant higher level when $V_{liq}$ switches from a dark period to a bright period is that it reduces the transient characteristics in the lipid bilayer, such as the RC time constant. By having more stabilized characteristics in the lipid bilayer, the measurement of the rate of change of $V_{ncap}$ during the integrating periods becomes more reliable.

As shown in FIG. 12, the reset signal is maintained at the high level at both the ending portion of a $V_{liq}$ dark period and the beginning portion of a $V_{liq}$ bright period. However, in some other embodiments, the reset signal may be maintained at the high level at the ending portion of a $V_{liq}$ dark period only. In some other embodiments, the reset signal may be maintained at the high level at the beginning portion of a $V_{liq}$ bright period only.

In some embodiments, the pre-charging period of frame 1202 is configurable. The pre-charging period, $t_{pre\text{-}charging}$, of frame 1202 is configured to a predetermined duration ranging from 50 microseconds to 1 millisecond seconds. In some embodiments, the pre-charging period of frame 1204 is configurable. The pre-charging period, $t_{pre\text{-}charging}$, of frame 1204 is configured to a predetermined duration ranging from 100 microseconds to 50 milliseconds. The pre-charging period that overlaps with the $V_{liq}$ dark period is between 50 microseconds to 25 milliseconds. The pre-charging period that overlaps with the $V_{liq}$ bright period is between 50 microseconds to 25 milliseconds.

It should be recognized that the steepness of the slope of $V_{ncap}$ is not drawn to scale in FIG. 12. The rate of decay in $V_{ncap}$ caused by the discharging of the capacitors may vary from frame to frame, and the different rates of decay may be used to analyze a molecule inside a nanopore. The rate of increase in $V_{ncap}$ caused by the charging of the capacitors may also vary from frame to frame, and the different rates of increase in $V_{ncap}$ may be monitored for calibrating the open-channel state, such as drift correction.

Figure 13:
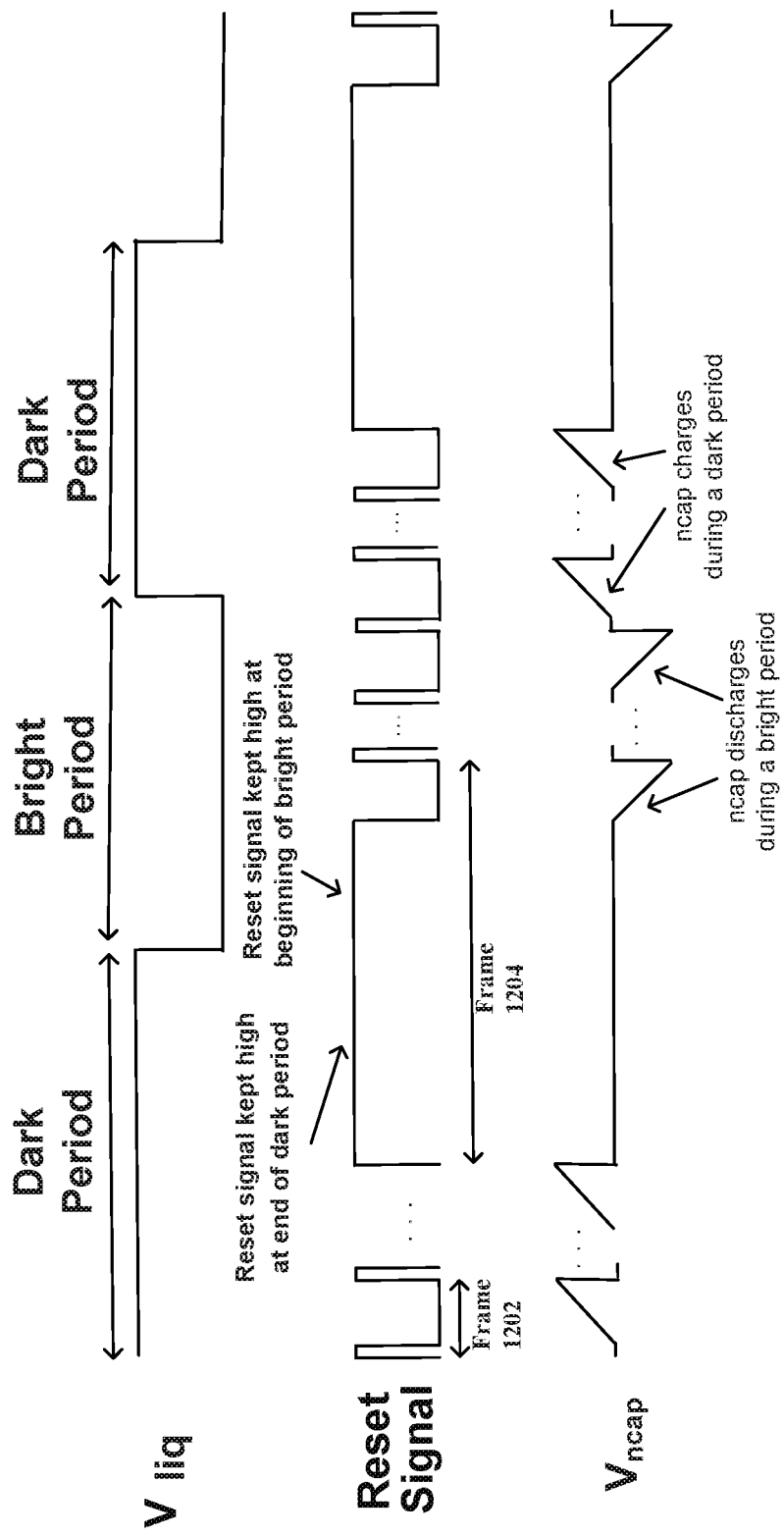
FIG. 13 illustrates another embodiment of a reset signal that is used to control the switch that connects or disconnects the voltage source to or from the membrane in a cell of the nanopore based sequencing chip.

For ease of illustration, only two integration periods are drawn within a single bright period of $V_{liq}$ in FIG. 12. Similarly, only one integration period is drawn within a single dark period of $V_{liq}$ in FIG. 12. However, it should be recognized that there may be tens or hundreds of integration periods within each bright period or dark periods, as illustrated in FIG. 13.

Figure 14:
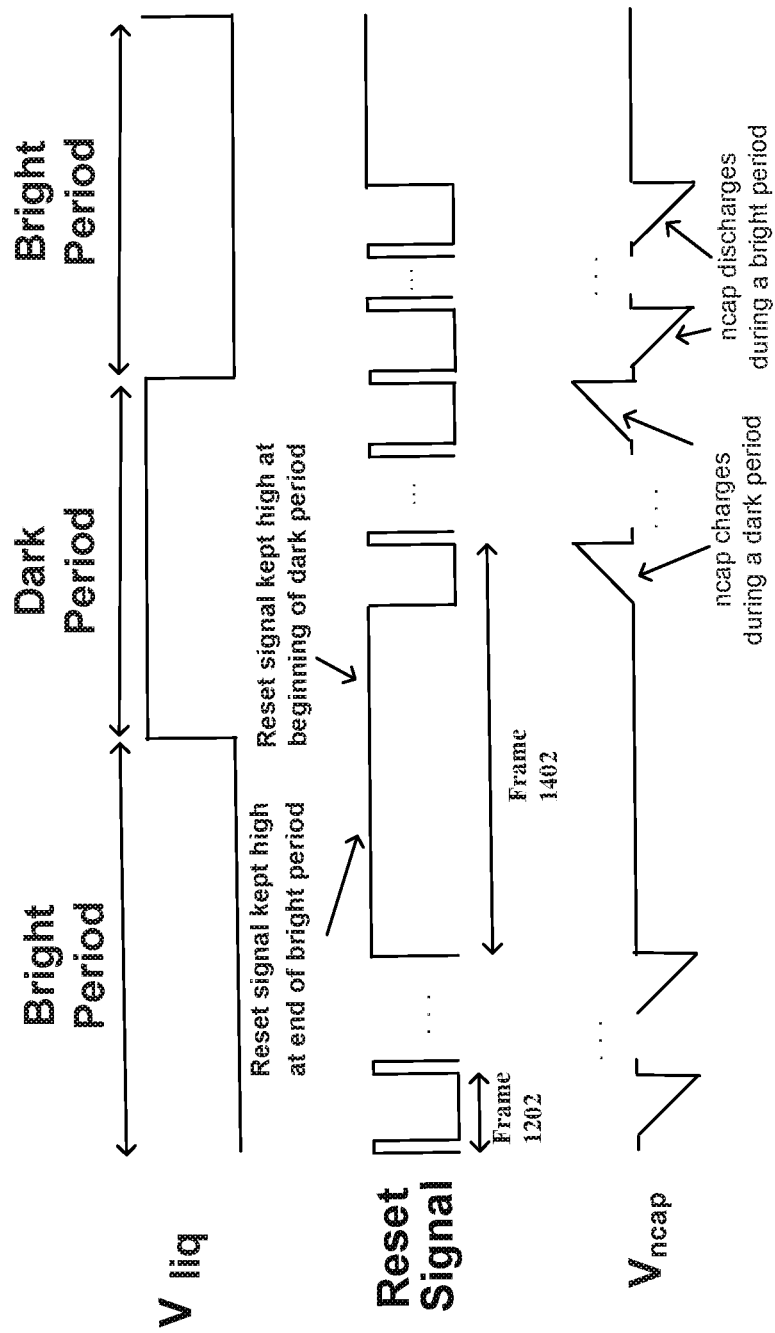
FIG. 14 illustrates yet another embodiment of a reset signal that is used to control the switch that connects or disconnects the voltage source to or from the membrane in a cell of the nanopore based sequencing chip.

FIG. 14 illustrates yet another embodiment of a reset signal that is used to control the switch that connects or disconnects the voltage source to or from the membrane in a cell of the nanopore based sequencing chip, such that the capacitor associated with the membrane is charged and discharged repeatedly. In some embodiments, the signals are provided by the circuitries shown in FIGS. 7A and 7B. The topmost plot of $V_{liq}$ is identical to the $V_{liq}$ plots in FIGS. 11 and 12. The middle plot shows another improved reset signal 703 that is used to control switch 701 that connects or disconnects voltage source $V_{pre}$ 705 to or from the membrane in a cell of the nanopore based sequencing chip. The bottom plot shows the voltage at the integrating capacitor ($V_{ncap}$) in response to the new improved reset signal and $V_{liq}$ as a function of time.

In contrast to the frames in FIG. 11, the duration of the frames in FIG. 14 are not kept constant over time. There are two types of frames in the reset signal. One type of frame (see e.g., frame 1202) is similar to the frames in FIG. 11. In these frames, the reset signal is maintained at a high level for a very brief $t_{pre-charging}$ period only, and as soon as the capacitors are pre-charged to $V_{pre}$, the reset signal is set to a low level to open the switch, allowing the voltage at integrating capacitor ncap 708 to float and change to a voltage other than $V_{pre}$. A second type of frame (see e.g., frame 1402) has longer pre-charging periods than the first type of frame. As shown in frame 1402, the reset signal is kept at the high level for a longer $t_{pre-charging}$ period. In particular, the reset signal is maintained at the high level during the ending portion of a $V_{liq}$ bright period and the beginning portion of a $V_{liq}$ dark period, such that there are no quick transitions of the reset signal when $V_{liq}$ switches from a bright period to a dark period.

By extending the pre-charging period in frame 1402, voltage source $V_{pre}$ 705 is connected to working electrode 714 for a longer period, and the voltage at the integrating capacitor, $V_{ncap}$, (see the bottom plot of FIG. 14) is maintained at $V_{pre}$ when $V_{liq}$ switches from a bright period to a dark period. In some embodiments, voltage source $V_{pre}$ 705 provides a constant positive voltage with a magnitude of 0.9 V. In other embodiments, $V_{pre}$ is a constant voltage selected from within a range of 0.7 to 1.2 V.

Maintaining $V_{ncap}$ at a constant higher level when $V_{liq}$ switches from a bright period to a dark period has its advantages. One advantage of maintaining $V_{ncap}$ at a constant higher level when $V_{liq}$ switches from a bright period to a dark period is that it reduces the transient characteristics to the lipid bilayer, such as the RC time constant. By having more stabilized characteristics in the lipid bilayer, the measurement of the rate of change of $V_{ncap}$ during the integrating periods becomes more reliable.

As shown in FIG. 14, the reset signal is maintained at the high level at both the ending portion of a $V_{liq}$ bright period and the beginning portion of a $V_{liq}$ dark period. However, in some other embodiments, the reset signal may be maintained at the high level at the ending portion of a $V_{liq}$ bright period only. In some other embodiments, the reset signal may be maintained at the high level at the beginning portion of a $V_{liq}$ dark period only.

In some embodiments, the pre-charging period of frame 1202 is configurable. The pre-charging period, $t_{pre-charging}$, of frame 1202 is configured to a predetermined duration ranging from 50 microseconds to 1 millisecond seconds. In some embodiments, the pre-charging period of frame 1402 is configurable. The pre-charging period, $t_{pre-charging}$, of frame 1402 is configured to a predetermined duration ranging from 100 microseconds to 50 milliseconds. The pre-charging period that overlaps with the $V_{liq}$ bright period is between 50 microseconds to 25 milliseconds. The pre-charging period that overlaps with the $V_{liq}$ dark period is between 50 microseconds to 25 milliseconds.

In some embodiments, the reset signal includes three types of frames—frames 1202, frames 1204, and frames 1402. By having both frames 1204 and 1402 in the reset signal, the voltage at the integrating capacitor, $V_{ncap}$, is maintained at $V_{pre}$ when $V_{liq}$ switches from a bright period to a dark period or vice versa.

Although the foregoing embodiments have been described in some detail for purposes of clarity of understanding, the invention is not limited to the details provided. There are many alternative ways of implementing the invention. The disclosed embodiments are illustrative and not restrictive.

All publications, patents, patent applications, and/or other documents cited in this application are incorporated by reference in their entirety for all purposes to the same extent as if each individual publication, patent, patent application, and/or other document were individually indicated to be incorporated by reference for all purposes.

The invention claimed is:

1. A method of analyzing a molecule in a nanopore, comprising:
    applying a liquid voltage to an electrolyte on a first side of a membrane, wherein the liquid voltage comprises a tag-reading period with a tag-reading voltage level that is configured to pull a tag of the molecule or a portion of the molecule into the nanopore in the membrane and an open-channel period with an open-channel voltage level that is configured to repel the tag or the portion of the molecule from the nanopore in the membrane;
    connecting a pre-charging voltage source to a capacitor and a working electrode on a second side of the membrane during a pre-charging time period, such that the capacitor and the working electrode are charged to a pre-charging voltage; and
    disconnecting the pre-charging voltage source from the capacitor and the working electrode during the tag-reading period, such that a voltage of the capacitor and a voltage of the working electrode may vary as a current flows through the nanopore in the membrane;
    wherein the pre-charging time period spans across a transition from the open channel period to the tag-reading period.

2. The method of claim 1, wherein the pre-charging time period overlaps with an ending portion of the open-channel period and a beginning portion of the tag-reading period.

3. The method of claim 1, wherein the pre-charging time period overlaps with a beginning portion of the open-channel period.

4. The method of claim 1, wherein the pre-charging time period overlaps with an ending portion of the tag-reading period.

5. The method of claim 1, wherein the pre-charging time period spans across a transition from the tag-reading period to the open-channel period.

6. The method of claim 1, wherein the pre-charging time period has a duration of 100 microseconds to 50 milliseconds.

7. The method of claim 1, wherein the pre-charging time period has a duration of 50 microseconds to 25 milliseconds.

8. A system, instrument or device for analyzing a molecule, comprising:
- a voltage source;
- a counter electrode coupled to the voltage source;
- a pre-charging voltage source;
- a capacitor that is configured to connect with the pre-charging voltage source;
- a working electrode that is configured configurable to connect with the pre-charging voltage source; and
- a controller configured to:
  - control the voltage source to apply a liquid voltage via the counter electrode to an electrolyte on a first side of a membrane, wherein the liquid voltage comprises a tag-reading period with a tag-reading voltage level that is configured to pull a tag of the molecule or a portion of the molecule into a nanopore in the membrane and an open-channel period with an open-channel voltage level that is configured to repel the tag or the portion of the molecule from the nanopore in the membrane;
  - connect the pre-charging voltage source to the capacitor and the working electrode on a second side of the membrane during a pre-charging time period, such that the capacitor and the working electrode are charged to a pre-charging voltage;
  - disconnect the pre-charging voltage source from the capacitor and the working electrode during the tag-reading period, such that a voltage of the capacitor and a voltage of the working electrode may vary as a current flows through the nanopore in the membrane; and
  - wherein the pre-charging time period spans across a transition from the open channel period to the tag-reading period; and
- a memory coupled to the controller and configured to provide the controller with instructions.

9. The system, instrument or device of claim 8, wherein the pre-charging time period overlaps with an ending portion of the open-channel period and a beginning portion of the tag-reading period.

10. The system, instrument or device of claim 8, wherein the pre-charging time period overlaps with a beginning portion of the open-channel period.

11. The system, instrument or device of claim 8, wherein the pre-charging time period overlaps with an ending portion of the tag-reading period.

12. The system, instrument or device of claim 8, wherein the pre-charging time period spans across a transition from the tag-reading period to the open-channel period.

13. The system, instrument or device of claim 8, wherein the pre-charging time period has a duration of 100 microseconds to 25 milliseconds.

* * * * *